United States Patent [19]
Arai et al.

[11] Patent Number: 5,168,101
[45] Date of Patent: Dec. 1, 1992

[54] SULFONAMIDE DERIVATIVES

[75] Inventors: Yoshinobu Arai, Osaka; Nobuyuki Hamanaka, Kyoto; Tohru Miyazaki, Osaka, all of Japan

[73] Assignee: Ono Pharmaceutical Co., Ltd., Osaka, Japan

[21] Appl. No.: 257,369

[22] Filed: Oct. 13, 1988

[30] Foreign Application Priority Data

Oct. 23, 1987 [JP] Japan .................................. 62-266501
Apr. 19, 1988 [JP] Japan .................................. 63-94545
Apr. 19, 1988 [JP] Japan .................................. 63-94546
Aug. 9, 1988 [JP] Japan .................................. 63-197180

[51] Int. Cl.$^5$ .................. C07C 143/72; C07C 143/78; A61K 31/00
[52] U.S. Cl. .................... 514/530; 514/538; 514/562; 514/604; 548/438; 548/334.1; 548/374.1; 560/12; 562/422; 562/430; 564/91; 564/93
[58] Field of Search ............... 560/12; 562/427, 430; 564/91, 93; 514/530, 538, 562, 604; 548/343, 378, 538

[56] References Cited

U.S. PATENT DOCUMENTS 4,654,357 3/1987 Nakane et al. ................. 560/2

FOREIGN PATENT DOCUMENTS 226346 6/1987 European Pat. Off. ............. 560/118

OTHER PUBLICATIONS

Mitra, The Synthesis of Prostaglandins, p. 241 (1977).

Primary Examiner—Robert Gerstl
Attorney, Agent, or Firm—Sughrue, Mion, Zinn, Macpeak & Seas

[57] ABSTRACT

A sulfonamide derivative of the general formula:

Tx—R$^1$  (I)

wherein, R$^1$ represents
(i) COOR$^{11}$,
(ii) CH$_2$OR$^{12}$ or
(iii) CONR$^{13}$R$^{14}$, Tx—represents

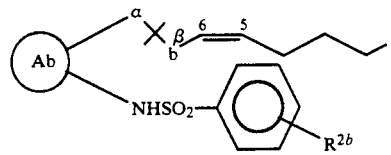

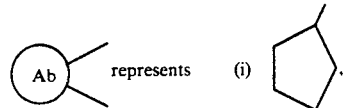 represents (i) 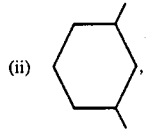 (A$_b$-1)

(ii) 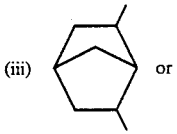 (A$_b$-2)

(iii) 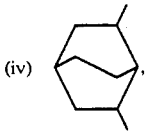 or  (A$_b$-3)

(iv) (A$_b$-4)

X$_b$ represents
(i) bond,
(ii) alkylene group of from 1 to 4 carbon atoms or
(iii) alkenylene group of from 2 to 4 carbon atoms (Abstract continued on next page.)

(with the proviso that $^{\alpha}$CH=CHCH$_2^{\beta}$ and $^{\alpha}$CH$_2$CH=CHCH$_2^{\beta}$ are excluded),
R$^{2b}$ represents
 (i) hydrogen atom,
 (ii) halogen atom or
 (iii) alkyl group of from 1 to 4 carbon atom(s), posses an antagonistic activity on TXA$_2$.

6 Claims, 3 Drawing Sheets

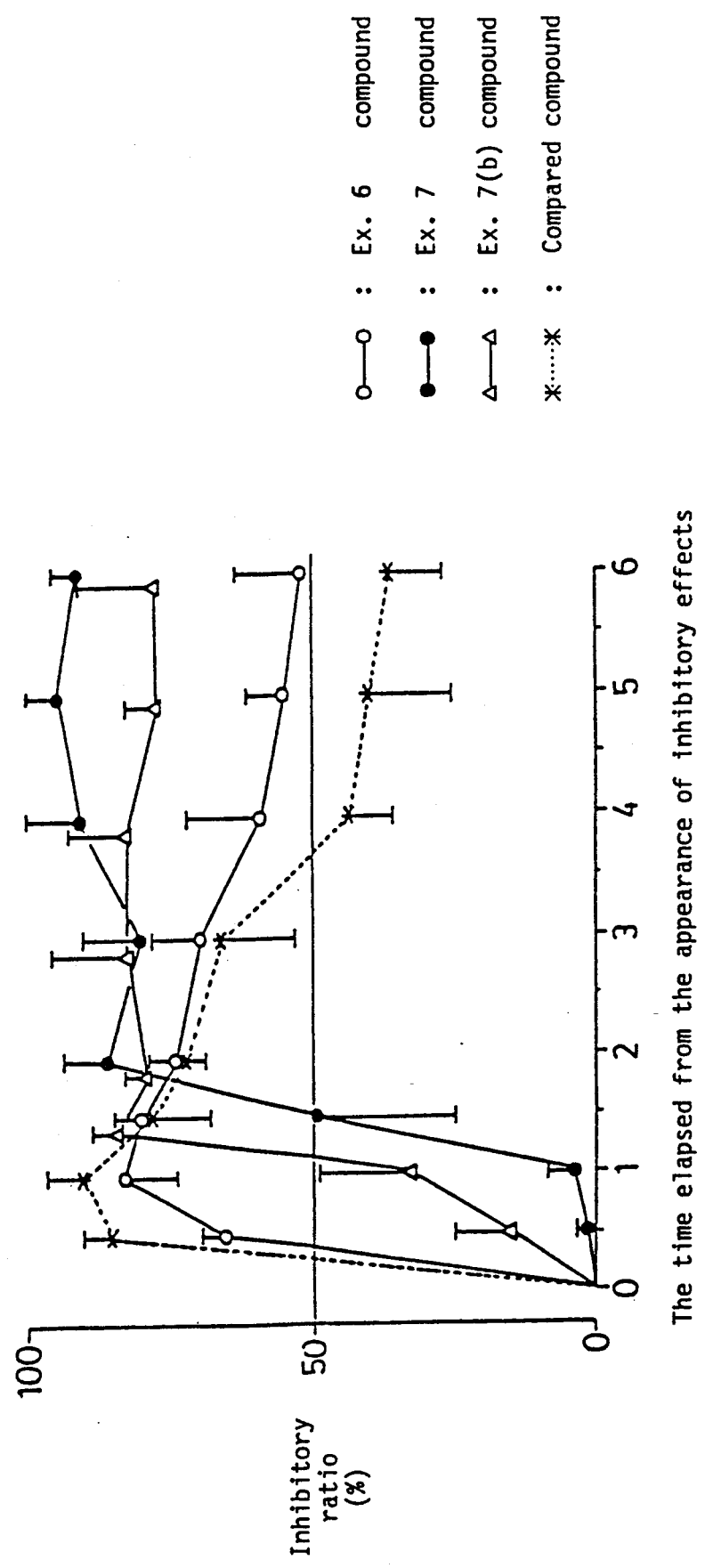

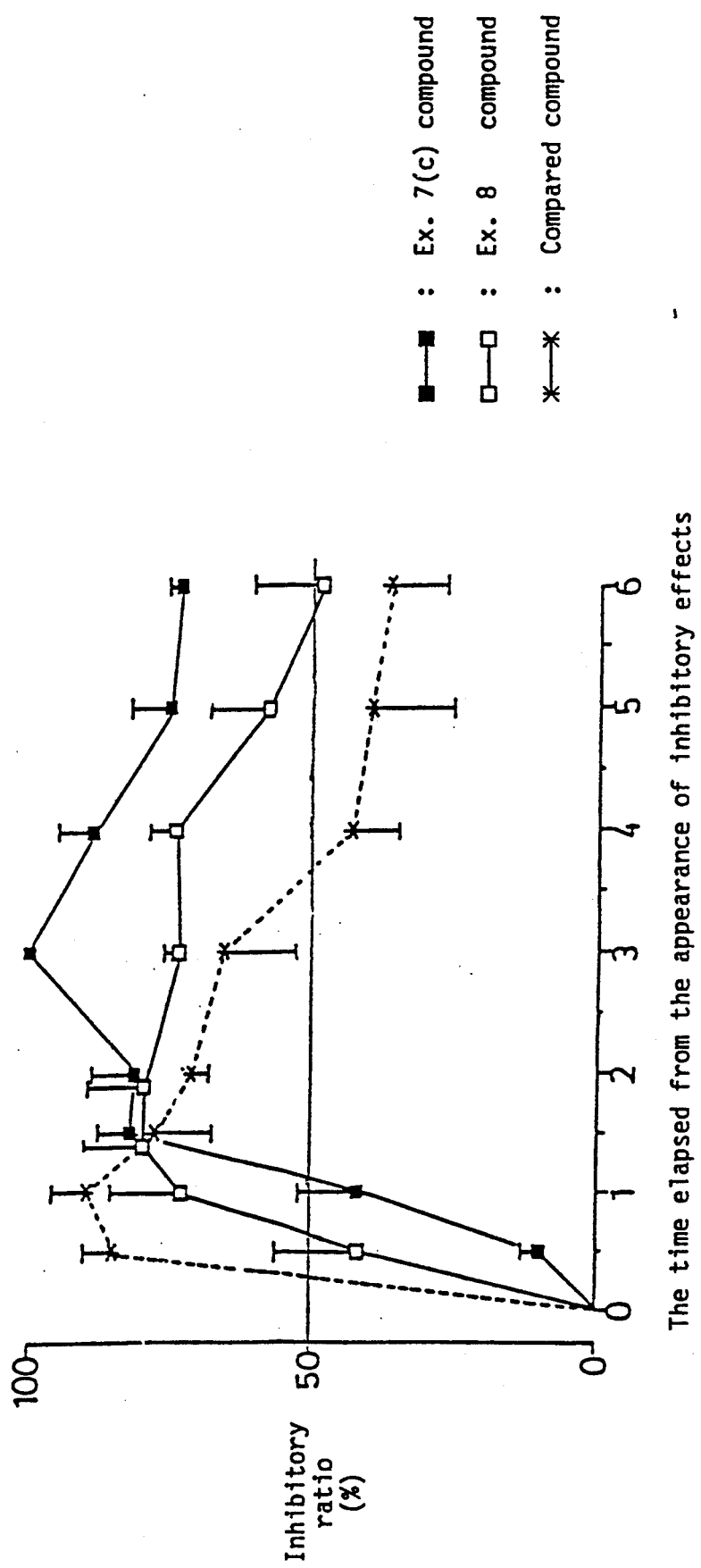
Fig. 2 Inhibitory ratio on increasing of blood pressure induced by $STA_2$ in guinea pig

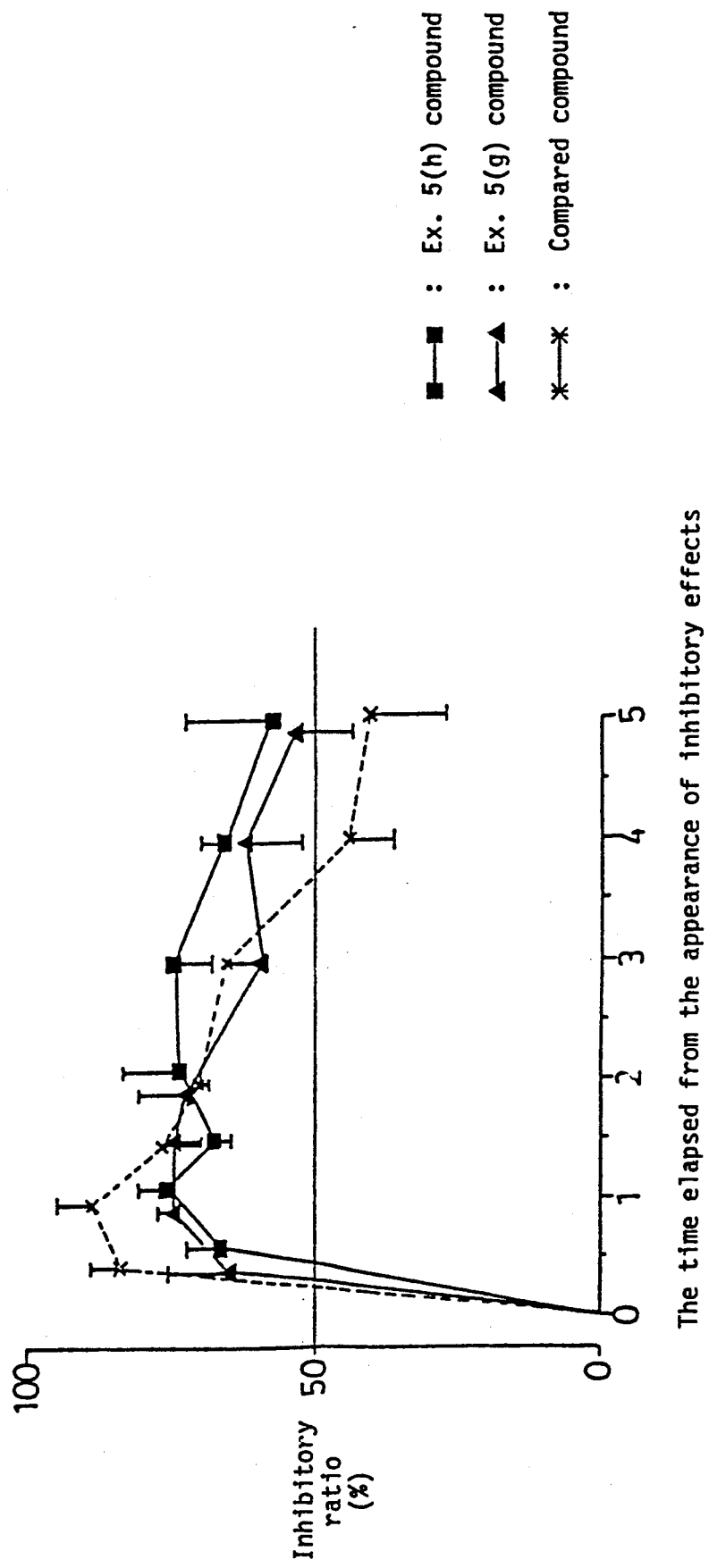
Fig. 3 Inhibitory ratio on increasing of blood pressure induced by STA$_2$ in guinea pig

SULFONAMIDE DERIVATIVES

DESCRIPTION

SUMMARY

This invention is related to novel sulfonamide derivatives.

More particularly, this invention is related to
(1) sulfonamide derivatives of the general formula

   (I)

(wherein, all of the symbols represent the same meaning as hereinafter defined.),
(2) processes for the preparation of them and
(3) treating agents containing them as an active ingredient.

BACKGROUND

In 1975, Hamberg et al discovered an unstable intermediate in the conversion of prostaglandin G2 into the hemiacetal derivative in platelets [Proc. Nat. Acad. Sci. U.S.A., Vol 72, No. 8 page 2,994 (1975)]. This intermediate has been named thromboxane $A_2$ and its structure has been proposed as follows:

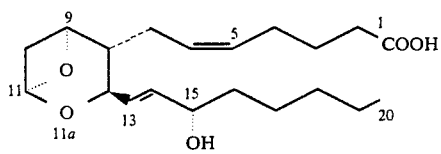   (a)

$TXA_2$ has been found to show various biological activities such as platelet aggregation, aorta contraction and thrombi formation and therefore is considered to be one of the causes by which diseases such as inflammation, thrombus and cardiac infarction are induced.

Some $TXA_2$ analogues are proposed as compounds having antagonistic activity on $TXA_2$; for example, compounds where the oxygen atoms at the 11a- and 9,11-epoxy-position of $TXA_2$ are replaced by carbon atoms [see Japanese Patent Kokai No. 55-143930], and compounds having a pinane skelton [Proc. Nat. Acad. Sci. U.S.A. Vol. 76, No. 6, page 2,566 (1979)]. The compounds described below which have a cyclopentane skeleton are also known.

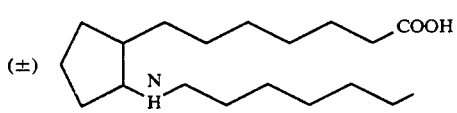   (b)

More recently, in the specification of GB No. 2184118, the carbocyclic sulfonamide derivatives of the general formula:

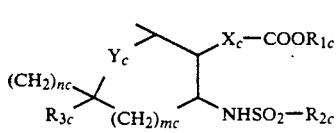   (c)

wherein $R_{1c}$ represents a hydrogen atom or lower alkyl group, $R_{2c}$ represents an alkyl group, substituted or unsubstituted aryl group, aralkyl group or heterocyclic ring, $R_{3c}$ represents a hydrogen atom or methyl group, Xc represents a alkylene group or alkenylene group substituted by one or more fluoro atom(s) or, containing one oxygen atom, sulfur atom or phenylene group, Yc represents a straight-chain or branched-chain alkylene group or alkenylene group, oxygen atom or sulfur atom, mc represents an integer of 0 or 1, and nc represents an integer of 0, 1 or 2 have been disclosed. The following compound was published by Bayer A. G. at 16th International Symposium on the Chemistry of National Products opened on May 29--Jun. 3, 1988.

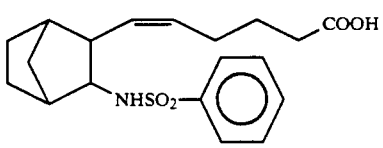   (d)

BRIEF DESCRIPTION OF DRAWINGS

FIG. 1, FIG. 2 and FIG. 3 show the change of rate which the compounds of the present invention inhibit increasing of blood pressure induced by $STA_2$ in guinea pig at time elapsed.

DISCLOSURE OF THE INVENTION

The present invention is related to sulfonamide derivatives of the general formula:

   (I)

wherein,
$R^1$ represents
(i) $COOR^{11}$,
(ii) $CH_2OR^{12}$ or
(iii) $CONR^{13}R^{14}$,
wherein
$R^{11}$ represents a hydrogen atom, alkyl group of from 1 to 20 carbon atom(s), carbocyclic ring unsubstituted or substituted by an alkyl or alkoxy group of from 1 to 4 carbon atom(s) or halogen atom, or steroid,
$R^{12}$ represents a hydrogen atom or $COR^{15}$,
$R^{13}$ and $R^{14}$ each represent a hydrogen atom or alkyl group of form 1 to 4 carbon atom(s) or $NR^{13}R^{14}$ represents an amino acid residue or heterocyclic ring, or
$R^{15}$ represents an alkyl group of from 1 to 4 carbon atom(s) or phenyl group,

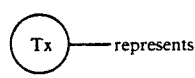 represents (i) 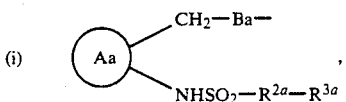   (A)

-continued (ii) 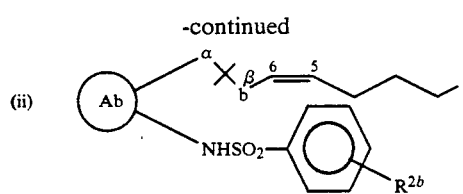

or (iii) 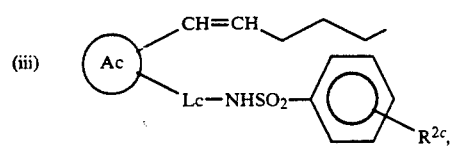

wherein Aa represents (i) 

(ii) 

(iii) 

(iv) 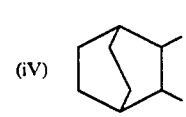

(v) 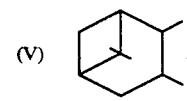

(vi) 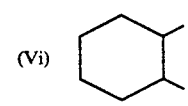

(vii) 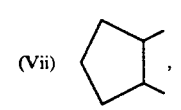

(viii) 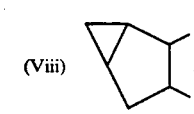

(ix) 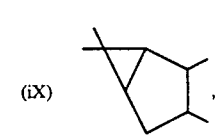

(X) 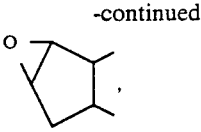 (Aa-10)

(Xi) 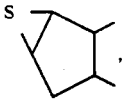 (Aa-11)

(C) Ba represents
(i) —CH$_2$—CH$_2$—(CH$_2$)m—  (Ba-1),
(ii) cis—CH=CH—(CH$_2$)m—  (Ba-2),
(iii) —CH$_2$—O—(CH$_2$)m—  (Ba-3),
(iv) —S—(CH$_2$)m—  (Ba-4) or
(v) —CH=CH—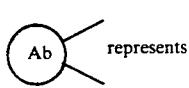  (Ba-5)

wherein m represents an integer of from 1 to 6, and the configuration of a double bond is E, Z or EZ and a phenylene group represents an o-, m- or p-phenylene group in the formula (Ba-5), R$^{2a}$ represents a bond or an alkylene group of from 1 to 4 carbon atom(s), R$^{3a}$ represents a carbocyclic or heterocyclic ring unsubstituted or substituted by from one to three of an alkyl group of from 1 to 4 carbon atom(s), alkoxy group of from 1 to 4 carbon atom(s), hydroxy group, carobyxl group, ciano group, halogen atom or nitro group, or R$^{2a}$ represents an alkyl group of from 1 to 12 carbon atom(s) together with R$^{3a}$, Ab represents (i) 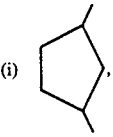 (A$_b$-1)

(ii) 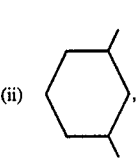 (A$_b$-2)

(iii) 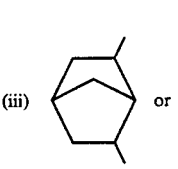 or (A$_b$-3)

(iv) 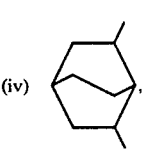 (A$_b$-4)

Xb represents
(i) bond,
(ii) alkylene group of from 1 to 4 carbon atoms or
(iii) alkyenlene group of from 2 to 4 carbon atoms (with the proviso that $\underline{^\alpha\text{-CH=CHCH}_2^\beta}$ and $\underline{^\alpha\text{-CH}_2\text{CH=CHCH}_2^\beta}$ are excluded), R$^{2b}$ represents
(i) hydrogen atom,
(ii) halogen atom or (iii) alkyl group of from 1 to 4 carbon atom(s), the configuration of a double bond between C₅ and C₆ in the general formula (B) is cis,

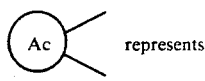 represents (i) , (Ac-1)

(ii) 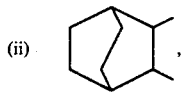, (Ac-2)

(iii) 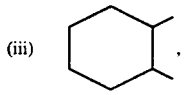, (Ac-3)

(iv) 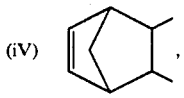, (Ac-4)

(V) 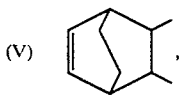, (Ac-5)

(Vi) 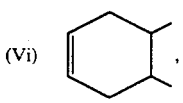, (Ac-6)

(Vii) 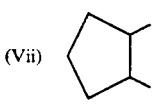, (Ac-7)

or (Viii) 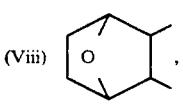, (Ac-8)

Lc represents an alkylene group of from 1 to 4 carbon atom(s).

R²ᶜ represents a hydrogen atom, alkyl group of from 1 to 4 carbon atom(s) or halogen atom, the configuration of a double bond between C₅ and C₆ in the general formula (c) is cis or trans, with the proviso that when

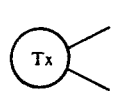

represents the general formula (A),
R¹¹ doesn't represents a hydrogen atom or alkyl group of from 1 to 20 carbon atom(s);
cyclodextrin clathrates thereof, or non-toxic salts thereof in case that R¹¹ represents a hydrogen atom or NR¹³R¹⁴ represents an amino acid residue, process for the preparation of them, and treating agent containing them as active ingredient.

The terms of alkyl group, alkylene group, alkenylene group and alkoxy group in description each symbol throughout the present specification including claims mean straight-chain or branched-chain alkyl group, alkylene group, alkenylene group and alkoxy group.

The configuration of double bonds in alkenylene groups are E, Z and E, Z mixtures. Isomers generated by asymmetric carbons existing in case that branched alkyl group are also included.

The presence of asymmetric centers leads, as is well known, to the existence of isomers. And all each optical isomers and all mixtures thereof are included in the general formula (I). For instance, a mixture of one optical isomer and enantiomer thereof, a racemic body which is an equivalent mixture especially and a mixture of one optical isomer and diastereomer thereof are also included.

In the structural formulae throughout the present specification dashed lines (⋯) indicate α-configuration, tapered lines (━) indicate β-configuration, and wavy lines (∿) indicate α- or β-configuration or mixture thereof.

In the general formula (I), the ring structures of the formula

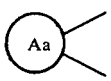

are named each and numbered at each position as follows.

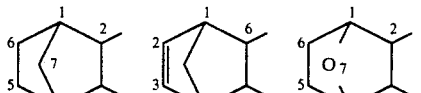

(Aa-1)    (Aa-2)    (Aa-3)

bicyclo[2.2.1]    bicyclo[2.2.1]    7-oxabicyclo
heptane    hept-2-ene    [2.2.1]heptane

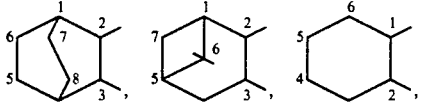

(Aa-4)    (Aa-5)    (Aa-6)

bicyclo[2.2.2]    6,6-dimethyl    cyclohexane
octane    bicyclo[3.1.1]
   heptane

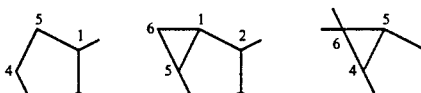

(Aa-7)    (Aa-8)    (Aa-9)

cyclopentane    bicyclo[3.1.0]    6,6-dimethyl
   hexane    bicyclo[3.1.0]
     hexane

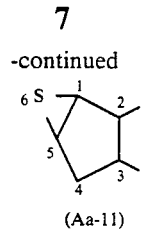

(Aa-10) 6-oxa-bicyclo [3.1.0]hexane  (Aa-11) 6-thiobicyclo [3.1.0]hexane

As will be apparent to those skilled in the art, ring structures described above have two [in case of the formulae (Aa-4), (Aa-6) and (Aa-7)] or four [in case of the formulae (Aa-1), (Aa-2), (Aa-3), (Aa-5), (Aa-8), (Aa-9), (Aa-10) and (Aa-11)] asymmetric carbon atoms. Namely they are 1-, 2-, 3- and 4- position carbon atoms in the formulae (Aa-1), (Aa-2) and (Aa-3), 2- and 3- position carbon atoms in the formulae (Aa-4), 1 and 2- position carbon atoms in the formulae (Aa-6) and (Aa-7) and 1-, 2-, 3- and 5- position carbon atoms in the formulae (Aa-5), (Aa-8), (Aa-9), (Aa-10) and (Aa-11).

And, the ring structure of the formula

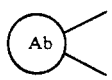

in the general formula (I) are named each and numbered at each position as follows.

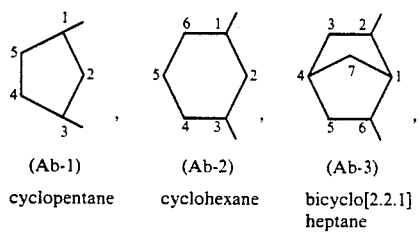

(Ab-1) cyclopentane  (Ab-2) cyclohexane  (Ab-3) bicyclo[2.2.1] heptane

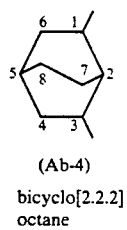

(Ab-4) bicyclo[2.2.2] octane

As will be apparent to those skilled in the art, ring structures described above have asymmetric carbon atoms. Namely, the ring structures of the formula (Ab-1) and (Ab-2) have two asymmetric carbon atoms (1- and 3-position carbon atoms), and the ring structures of the formula (Ab-3) and (Ab-4) have four asymmetric carbon atoms (1-, 2-, 4- and 6-position carbon atoms).

And, the ring structures of the formula

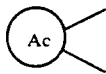

in the general formula (I) are named each and numbered at each position as follows.

As will be apparent to those skilled in the art, ring structures described above have two [in case of the formula (Ac-2), (Ac-3), (Ac-6) and (Ac-7)] or four [in case of the formula (Ac-1), (Ac-4),

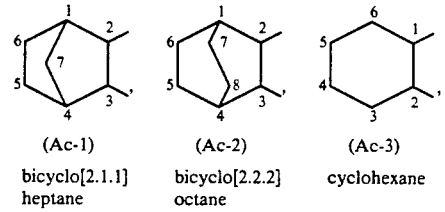

(Ac-1) bicyclo[2.1.1] heptane  (Ac-2) bicyclo[2.2.2] octane  (Ac-3) cyclohexane

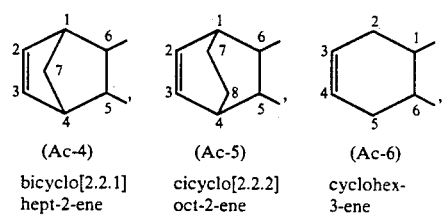

(Ac-4) bicyclo[2.2.1] hept-2-ene  (Ac-5) cicyclo[2.2.2] oct-2-ene  (Ac-6) cyclohex-3-ene

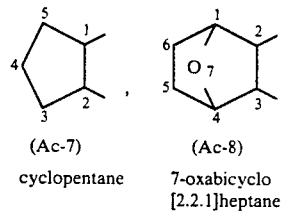

(Ac-7) cyclopentane  (Ac-8) 7-oxabicyclo [2.2.1]heptane (Ac-5) and (Ac-8]asymmetric carbon atoms. Namely, they are 2- and 3-position carbon atoms in the formula (Ac-2), 1- and 2-position carbon atoms in the formula (Ac-3) and (Ac-7), 1- and 6- position carbon atoms in the formula (AC-6), 1-, 2-, 3- and 4-position carbon atoms in the formula (Ac-1) and (Ac-8), 1-, 4-, 5- and 6-position carbon atoms in the formula (AC-4) and (Ac-5).

The presence of asymmetric centers leads, as is well known, to the existence of isomers. And all optical isomers and all mixtures thereof are included in the general formula (I). For instance, a mixture of one optical isomer and enantiomer thereof, a racemic body which is an equivalent mixture especially and a mixture of one optical isomer and diastereomer thereof are also included.

Steric structures of each isomers and racemic bodies are shown by absolute configuration, for example, as follows.

(i) in case of an optically active substance:

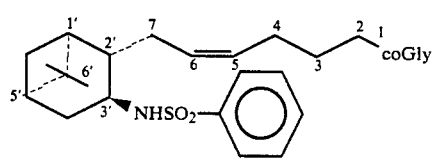

amide of (5Z)-7-[(1S, 2S, 3S, 5R)-3-benzenesulfonylamino-6,6-dimethylbicyclo [3.1.1]heptan-2-yl]hept-5-enoic acid and glycine

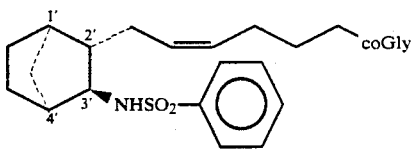

amide of (5Z)-7-[(1R, 2S, 3S, 4S)-3-benzenesulfonylaminobicyclo[2.2.1]heptan-2-yl]hept-5-enoic acid and glycine (ii) in case of a racemic body:

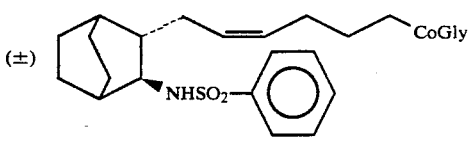

amide of (5Z)-7-[(2S*, 3S*)-3-benzenesulfonylaminobicyclo[2.2.2]octan-2-yl]hept-5-enoic acid and glycine In the general formula (I), alkyl groups of from 1 to 20 carbon atom(s) shown by $R^{11}$ are methyl, ethyl, propyl, butyl, pentyl, hexyl, heptyl, octyl, nonyl, decyl, undecyl, dodecyl, tridecyl, tetradecyl, hexadecyl, heptadecyl, octadecyl, nonadecyl, icosyl and isomeric groups thereof. Steroids shown by $R^{11}$ are the compounds which have steroid skeleton substituted by various substituents, for example, cholesterol. Preferable $R^{11}$ are methyl, ethyl, propyl, isopropyl, 1-ethylpropyl, hexyl, octyl, decyl, dodecyl group and cholesterol. It's also preferable that $R^{11}$ is a hydrogen atom. Carbocyclic rings in the group shown by $R^{11}$, are mono-, bi- or tri- aromatic carbocyclic rings containing not more than 15 carbon atoms which may be partially or fully saturated.

The rings are, for example, benzene, naphthalene, indene, aqulene, fluorene, phenanthrene, anthracene, acenaphthylene, biphenylene ring and the rings which may be partially or fully saturated thereof. Preferable rings are benzene and cyclohexane. Alkyl groups of from 1 to 4 carbon atom(s) shown by substituents in groups which $R^{11}$ represent are methyl, ethyl, propyl, butyl and isomeric groups thereof and alkoxy groups of from 1 to 4 carbon atom(s) are methoxy, ethoxy, propoxy, butoxy and isomeric group thereof and halogen atoms are fluorine, chlorine, iodine and bromine atom. Preferable substituents in $R^{11}$ are methyl and isopropyl group. Carbocyclic rings in $R^{11}$ are also preferable to be unsubstituted.

In general formula (I), preferable $R^{12}$ are hydrogen atom, acetyl and benzoyl group.

In general formula (I), amino acid residues shown by $NR^{13}R^{14}$ mean α-amino acid residues wherein a hydrogen atom in the amino group is removed.

For example, they are glycine, alanine, valine, isoleucine, leucine, serin, threonine, proline, asparagine, glutamine, methionine, phenylalanine, tyrosine, aspartic acid, glutamic acid and lysine residue.

In the general formula (I), heterocyclic rings shown by $NR^{13}R^{14}$ are mono-, bi- or tri- aromatic heterocyclic rings containing not more than 15 carbon and hetero atoms which may be partially or fully saturated. For example, they are pyrrole, oxazole, imidazole, pyrazole, pyridine, pyrimidine, pyridazine, pyrimidine, pyrazine, pyrroline, pyrrolidine or imidazolidine and pyrrolidine is preferable.

Preferable ring structures shown by

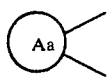

are the bridged ring shown by the formula (Aa-1), (Aa-2), (Aa-3), (Aa-4) and (Aa-5). Especially preferable group is a bridged carbocyclic ring shown by the formula (Aa-1).

In the general formula (I), out of groups represented by Ba, groups of the formulal (Ba-2) and (Ba-5), having a double bond are preferred. Especially preferable group is a group shown by the formula (Ba-2).

In the general formula (I), groups shown by the formula $—(CH_2)_m—$ represent methylene, ethylene, trimethylene, tetramethylene, pentamethylene and hexamethylene group. Preferable group is a trimethylene group.

In the general formula (I), groups shown by $R^{2a}$ represent a bond and an alkylene group of from 1 to 4 carbon atom(s). Preferable group is a bond.

In the general formula (I), groups shown by $R^{3a}$ represent carbocyclic and heterocyclic rings unsubstituted and substituted by alkyl group of from 1 to 4 carbon atom(s), alkoxy group of from 1 to 4 carbon atom(s), nitro group, hydroxy group, carboxyl group, cyano group or halogen atom. Carbocyclic rings described herein are mono-, bi- or tri- aromatic carbocyclic rings containing not more than 15 carbon atoms which may be partially or fully saturated. Heterocyclic rings described herein are mono-, bi- or tri- aromatic heterocyclic rings containing not more than 15 carbon and hetero atoms which may be partially or fully saturated. For example they are benzine, naphthalene, pyridine ring. Benzine ring is preferable. Especially preferable $R^3$ is 4-methylphenyl group.

Alkyl groups of from 1 to 12 carbon atom(s) which $R^{2a}$ and $R^{3a}$ represent together, are methyl, ethyl, propyl, butyl, pentyl, hexyl, heptyl, octyl nonyl, decyl, undecyl, dodecyl and isomeric groups thereof. All groups are preferable.

Preferable ring structures shown by

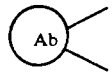

are the monocarbocyclic ring shown by (Ab-1) and (Ab-2).

In the general formula (I), alkylene groups of from 1 to 4 carbon atom(s) shown by Xb are methylene, ethylene, trimethylene, tetramethylene groups and isomeric groups thereof. Preferable group are methylene and ethylene group.

In the general formula (I), alkenylene groups of from 2 to 4 carbon atom(s) shown by Xb are vinylene, propenylene, butenylene, butadienylene group and isomeric groups thereof. Preferable group is a vinylene group. Preferable Xb are a bond, methylene, ethylene and vinylene group. Especially preferable group is a bond.

In the general formula (I), alkyl groups of from 1 to 4 carbon atom(s) are methyl, ethyl, propyl, butyl group and isomeric groups thereof. Halogen atom shown by $R^{2b}$ are fluorine, chlorine, iodine and bromine atom. All groups are preferable and $R^{2b}$ are also preferable to represent a hydrogen atom.

In the compounds of the general formula (I), of the present invention, ring structures shown by

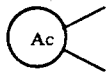

have many kinds of stereoisomers (geometrical and optical isomer).

The present invention includes all isomers as described hereinbefore. Preferable ring structures of

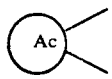

are the ring in which two side chains combine with in trans such as

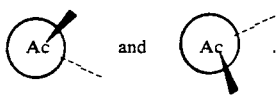

Especially preferable ring structures are the ring structures shown by

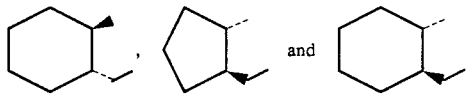

In the general formula (I), alkylene groups of from 1 to 4 carbon atom(s) shown by Lc are methylene, ethylene, trimethylene and tetramethylene. Preferable groups are methylene and ethylene group.

In the general formula (I), alkyl groups of from 1 to 4 carbon atom(s) shown in $R^{2c}$ are methyl, ethyl, propyl, butyl and isomeric groups thereof. Preferable group is a methyl group. Halogen atoms shown by $R^{2c}$ are chlorine, fluorine, bromine and iodine atom. A bromine atom is preferable.

Cyclodextrin Clathrates

The cyclodextrin clathrates of the compounds shown by the general formula (I), of the present invention may be prepared with using α-, β- or γ- cyclodextrin or a mixture thereof, by the method described in the specification of British Patent Nos. 1,351,238 or 1,419,221.

By converting into cyclodextrin clathrates, the stability of the compounds of the formula (I) can be increased.

Salts

The compounds in which $R^{11}$ represents a hydrogen atom or $NR^{13}R^{14}$ represents an amino acid among the compounds of the general formula (I), of the present invention may be converted into the corresponding salts. Non-toxic and water-soluble salts are preferable. Suitable salts, for example, are as follows: salts of alkaline metal (sodium, potassium etc.), salts of alkaline earth metal (calcium, magnesium etc.), ammonium salts, salts of pharmaceutically acceptable organic amines (tetramethylammonium, triethylamine, methylamine, dimethylamine, cyclopentylamine, benzylamine, phenethylamine, piperidineamine, monoethanolamine, diethanolamine, tris(hydroxymethyl)amine, lysine, arginine, N-methyl-D-glucamine etc.).

Comparison with prior art

The compounds of the general formula (I), of the present invention, are perfectly novel compounds which have quite different chemical structures from prior known compounds.

Described concretely,
(1) the compounds in which

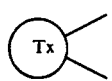

represents the formula (B) have structures in which two side chains (the side chain including $R^1$ group and the side chain including $NHSO_2$ group) bond to 1- and 3-position carbon atoms to each other, (2) the compounds in which

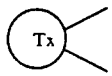

represents the formula (C) have structures which $NHSO_2$ group bond combines to the carbocyclic ring across a alkylene chain, (3) the compounds in which

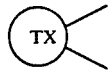

represents the formula (A) are carboxylic acid derivatives such as esters with carbocyclic rings and steroids, alcohols and amides with amino acids and heterocyclic ring in the present invention, though the prior compounds in which represents the formula (A) are only carboxylic acids and alkyl esters.

Accordingly, the compounds of the present invention are novel compounds having different structures from the prior compounds. It can be unexpected that the compounds which have different structures from the prior $TXA_2$ antagonists as described above, also possess an antagonistic effect against $TXA_2$.

Moreover, the compounds of the general formula (I), of this invention possess more useful features in pharmacodynamic effect than the prior $TXA_2$ antagonists.

Described concretely, the compounds of the present invention possess an antagonistic activity against $TXA_2$ and a part of them possess significantly stronger activity than the prior compounds of the formula (b) and (c). And, the inventors have confirmed that some compounds of the present invention hardly possess a side effect i.e. an agonistic activity against $TXA_2$ (effect of increasing of blood pressure) which the prior $TXA_2$ antagonists possess. It could be unexpected that the compounds prepared by changing the structures of the prior TXA$_2$ antagonists as described above possess different activities from the prior TXA$_2$ antagonists, until the inventors synthesized them and confirmed their activities.

Process for the preparation for the compounds of the present invention

According to the present invention, the compounds of the general formula (I), of the present invention may be prepared by the steps described hereinafter.

Step 1:

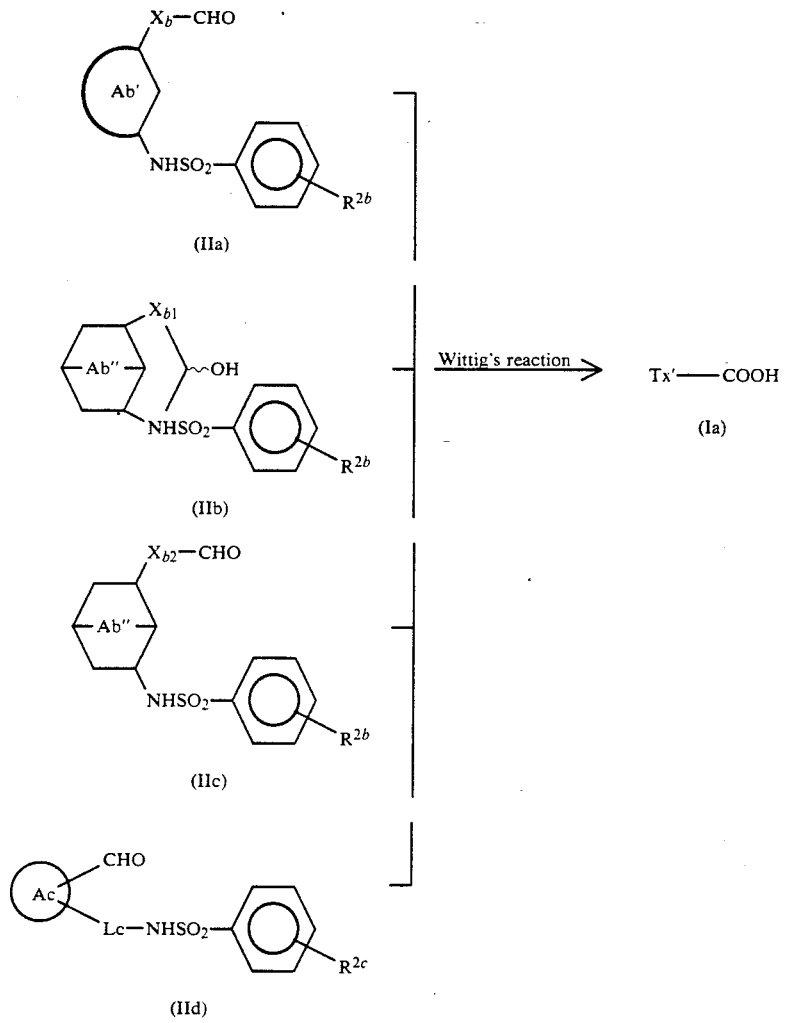

Step 2:

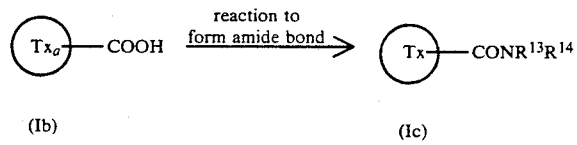

(Ib) (Ic)

Step 3:

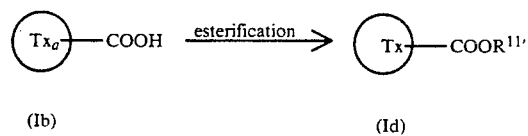

(Ib) (Id)

Step 4:

-continued

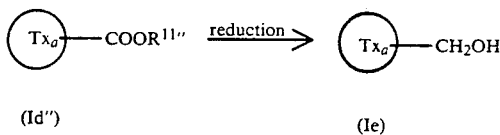

(Id'')  (Ie)

Step 5:

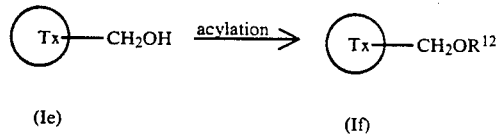

(Ie)  (If)

Step 6:

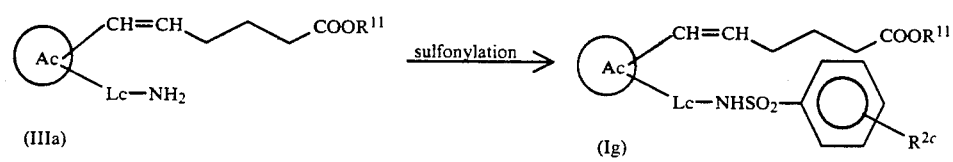

(IIIa)  (Ig)

Step 7:

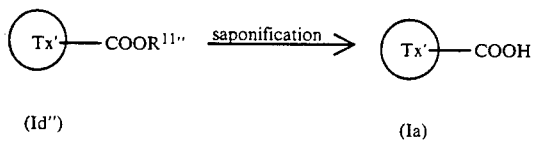

(Id''')  (Ia)

Wherein,

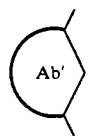

represents a group shown by the formulae $(A_b\text{-}1)$ or $(A_b\text{-}2)$,

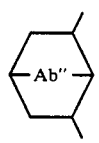

represents a group shown by the formulae $(A_b\text{-}3)$ or $(A_b\text{-}4)$, $X_{b1}$ represents a bond or methylene group, with the proviso that $X_{b1}$ and nitrogen atom in

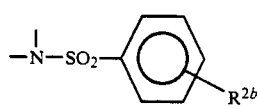

combine to ring structure in syn each other, $X_{b2}$ represents the same meaning as $X_b$, with the proviso that $X_{b2}$ and nitrogen atom in

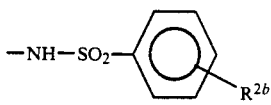

combine to ring structure in anti each other in the case that $X_{b2}$ represents a bond or methylene group,

represents a group shown by the formulae (B) or (C),

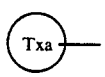

represents the formula (A), (B) and (C), $R^{11'}$ represents an alkyl group of from 1 to 20 carbon atom(s), carbocyclic ring unsubstituted or substituted by an alkyl or alkoxy group of from 1 to 4 carbon atom(s) or halogen atom, or steroid, $R^{11''}$ represents an alkyl group of 1 to 8 carbon atom(s) and the other symbols represent the same meaning as described hereinbefore.

Describing each step briefly,

Step 1 is a well known reaction such as Wittig's reaction. For example, it may be carried out by reacting an aldehyde of the general formula (IIa), (IIc) or (IId) or an aminoacetal of the general formula (IIb) and a phosphonium salt of the formula:

$$\left(\underset{3}{\bigcirc}\right)\overset{\oplus}{-}P-CH_2-(CH_2)_3-COOH.\overset{\ominus}{Y^1} \quad (1)$$

(wherein, $Y_1$ represents a halogen atom.) in the presence of a strong base (Potassium tert-butoxide, lithiumn diisopropylamide, sodium hydride etc), in an inert organic solvent (toluene, tetrahydrofuran, dimethylsulfoxide etc.), at from $-78°$ C. to a room temperature.

Step 2 is the reaction to form amide bond. For example, the reaction may be carried out by reacting (i) with using a corresponding amine shown by the formula $H_2NR^{13}$ ($R^{13}$ represents the same meaning as described hereinbefore), in an inert organic solvent (methylene chloride, toluene etc), at a temperature of from 0° C. to 40° C., after reacting oxalyl chloride, (ii) with using a corresponding amine shown by the formula $H_2NR^{13}$ ($R^{13}$ represents the same meaning as described hereinbefore), e.g. 2-chloro-1-methylpyridinium iodide and tertiary amine (triethylamine etc), in an inert organic solvent (methylene chloride etc), at a temperature of from 0° C. to 40° C. In case that an amine shown by the formula $HNR^{13}R^{14}$ represents an amino acid, the reaction is carried out by reacting the compounds in which a carboxyl group in an amine acid is protected by an appropriate alkyl group, or the compounds in which an amino group having no connection to the reaction is protected by a tert-butoxycarbonyl group (boc group) or a benzyloxy carbonyl group (cbz group), and then hydrolyzing with using an acid (trifluoroacetic acid etc.) or an alkali (sodium hydroxide etc.) to remove a protecting group.

Step 3 is esterification. For example, it may be carried out by (i) using the corresponding diazoalkane in an inert organic solvent (diethylether, methylene chloride etc.) at a temperature of from 0° C. to 40° C. (ii) using the corresponding alkylhalide in the presence of a base (sodium carbonate etc.) in an inert organic solvent (acetone, dimethylsulfoxide etc.) at a temperature of from $-10°$ C. to 80° C., or (iii) reacting an acid chloride corresponding to the acid of the formula (Ib) and the desired alcohol at a temperature of from $-10°$ C. to 40° C.

Step 4 is reduction. It may be carried out by reacting with using lithium aluminum hydride or diisobutyl aluminum hydride, in an inert organic solvent (tetrahydrofuran, diethylether, lower alkanol etc.), at from $-78°$ C. to a room temperature.

Step 5 is acylation. It may be carried out by reacting an acylhalide or acid anhydride in the presence of a tertiary amine (pyridine, triethylamine) in an inert organic solvent (diethylether, tetrahydrofuran, methylene chloride) or no solvent at a temperature of from $-20°$ C. to 50° C.

Step 6 is sulfonylation. For example, it may be carried out in the presence of Lewis' base (triethylamine, pyridine, dimethylaminopyridine etc.) at a temperature of from $-40°$ C. to 50° C.

Step 7 is saponification. For example, it is carried out with using an aqueous solution of an alkali (sodium hydroxide, potassium carbonate, lithium hydroxide etc.) in a water-soluble organic solvent (tetrahydrofuran, methanol, ethanol etc.) usually at a temperature of from $-10°$ C. to 100° C.

Process for the preparation of starting material

The compounds of the general formula:

$$\text{(Tx'')}-COOH \quad (Ib-1)$$

(wherein, $$\text{(Tx'')}-$$

represents the formula (A).)
in the compounds used as the starting materials, are described in the specification of British Patent Publication No. 2184118 and they may be prepared by the following method.

Step 1'-1:

$$\text{(Aa')}\begin{matrix}CH_2-Ba-COOH\\ \\ NH_2\end{matrix} \xrightarrow{\text{sulfonylation}}$$

(V)

$$\text{(Aa')}\begin{matrix}CH_2-Ba-COOH\\ \\ NHSO_2-R^{2a}-R^{3a}\end{matrix}$$

(Ib-1'''')

Step 1'-2:

$$\text{(Tx'')}-COOR^{11'''} \xrightarrow{\text{saponification}} \text{(Tx'')}-COOH$$

(Id-1) \qquad\qquad (Ib-1)

Step 2':

$$\text{(Aa')}\begin{matrix}CH_2-CHO\\ \\ NHSO_2-R^{2a}-R^{3a}\end{matrix} \xrightarrow{\text{Wittig's reaction}}$$

(VI)

$$\text{(Aa')}\begin{matrix}CH_2-Ba'-COOH\\ \\ NHSO_2-R^{2a}-R^{3a}\end{matrix}$$

(Ib-1')

Step 3':

$$\text{(Aa'')}\begin{matrix}\diagup\!\!\diagdown\!\!\diagup\!\!\diagdown(CH_2)_{m-1}-COOH\\ \\ NHSO_2-R^{2a}-R^{3a}\end{matrix} \xrightarrow{\text{reduction}}$$

(VII)

-continued

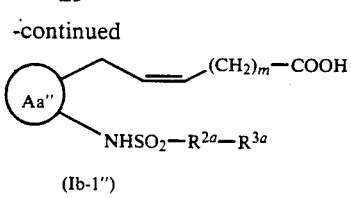
(Ib-1″)

Step 4':

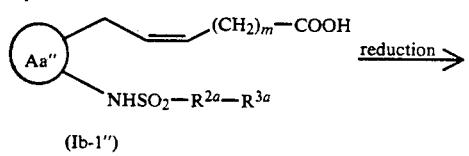
(Ib-1″)

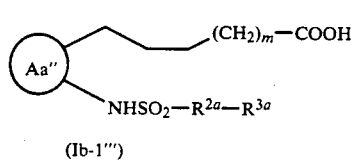
(Ib-1‴)

(wherein

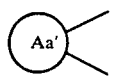

represents a group of the formulae (Aa-1), (Aa-2), (Aa-3), (Aa-4), (Aa-5), (Aa-6) or (Aa-7),

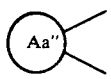

represents a group of the formulae (Aa-1), (Aa-3), (Aa-4), (Aa-6) or (Aa-7),

Ba' represents a group of the formulae (Ba-2) or (Ba-5), the other symbols represent the same meaning as described hereinbefore, with the proviso that the configurations of two double bond in formula (5) are each E, Z or EZ.).

Explaining each reaction step in detail,

Step 1'-1 is sulfonylation reaction. For example, it may be carried out with using a sulfonyl halide of the formula:

$$X-SO_2-R^{2a}-R^{3a} \quad (2)$$

(wherein, X represents a halogen atom and the other symbols represent the same meanings as defined hereinbefore) in the presence of Lewis' base (tertiary amine such as triethylamine, pyridine, dimethylaminopyridine etc) as a stimulator, in an inert organic solvent (methylene chloride etc), at a temperature of from −40° C. to 50° C. (preferably, at from 0° C. to room temperature).

Step 1'-2 is saponification. For example, it is carried out with using an aqueous solution of an alkali (sodium hydroxide, potassium carbonate, lithium hydroxide etc.), in a water-soluble organic solvent (tetrahydrofuran, methanol, ethanol etc.) usually at a temperature of from −10° C. to 100° C.

Step 2' is a well known reaction such as Witting's reaction. For example, it may be carried out by reacting an aldehyde of the general formula (IV) and a phosphonium salt of the general formula:

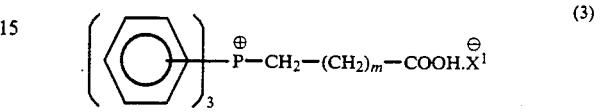 (3)

or

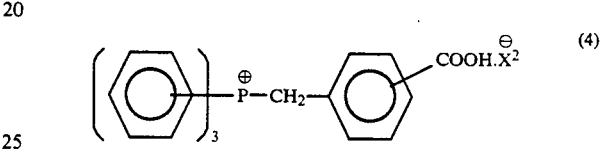 (4)

(wherein, $X^1$ and $X^2$ each represent a halogen atom and m represents the same meaning as defined hereinbefore) in the presence of a strong base (potassium tert-butoxide, lithium diisopropylamide, sodium hydride etc), in an inert organic solvent (toluene, tetrahydrofuran, dimethylsulfoxide etc.), at from −78° C. to a room temperature.

Step 3' may be carried out by reacting with using methyl benzoate chromium tricarbonyl, as catalyst, in an inert organic solvent (acetone etc.), in an atmosphere of hydrogen, at from 70 to 120 atmospheres, at from 100° C. to 150° C.

Step 4' is reduction reaction. For example, it may be carried out in the presence of hydrogenation catalyst (palladium-carbon, nickel etc), in an alkanol, in an atmosphere of hydrogen, usually at ordinary temperature and pressure or by raising a little the temperature and atmosphere as occasion demands.

The compounds of the formulae (V), (VI) and (VII) using as starting materials partially include known compounds. New compounds of the present invention also may be prepared by a known method. For example, the compounds of the formula (V) and (VI) which involve formula (Aa-5) may be prepared as follows. And the process of preparation for a part of the compounds shown by the formula (V) was described in the specification of Japanese Patent Kokai No. 61-49, i.e. European Patent Publication No. 0171146.

In the following formulae, THP represents tetrahydropyran-2-yl group and the other groups represent the same meaning as defined hereinbefore.

Scheme [A]

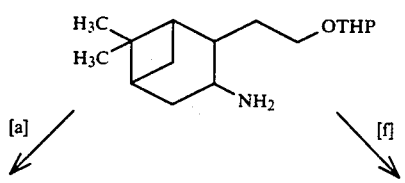

Scheme [A]

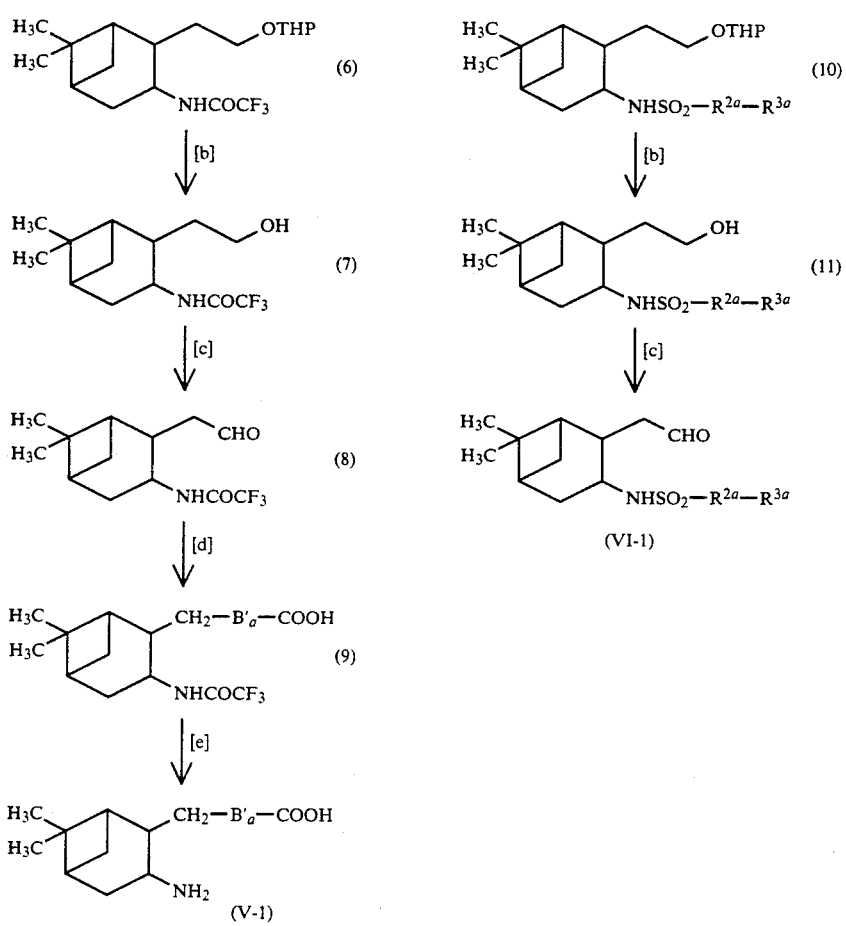

Explaining each step briefly, step [a] is the introduction of a protecting group (trifluoroacetyl group) into an amino group. For example, it may be carried out with using anhydrous trifluoroacetic acid, in the presence of a tartiary amine (pyridine etc.), in an inert organic solvent (methylene chloride etc.).

Step [b] is elimination reaction of protecting group of hydroxyl group. For example, it may be carried out with using an acid (p-toluene sulfonic acid, acetic acid etc.), in an organic soluvent (methanol-water etc.).

Step [c] is oxidation. For example, it may be carried out with using an oxidizing agent (oxalyl chloride-dimethylsulfoxide, sulfur trioxide-pyridine complex, dimethylsulfoxide etc), in the presence of a tertiary amine (triethylamine etc.), in a suitable organic solvent (methylene chloride, dimethylsulfoxide etc.).

Step [d] is Wittig's reaction. It may be carried out with using a phosphorane compound of the formula (3) or (4), by the same procedure as described in step 2'.

Step [e] is saponification. For example, it is carried out (i) with using an aqueous solution of an alkali (sodium hydroxide, potassium carbonate, lithium hydroxide etc.), in a water—soluble organic solvent (tetrahydrofuran, methanol, ethanol etc.), or (ii) with using an alkali described hereinbefore, under the anhydrous condition, in an alkanol (methanol, ethanol etc). These reactions may be carried out usually at a temperature of from $-10°$ C. to $100°$ C.

Step [f] is sulfonylation reaction. It may be carried out by the same procedure as described step 1'-1.

The compound of the formula (5) may be prepared as follows.

Scheme [B]

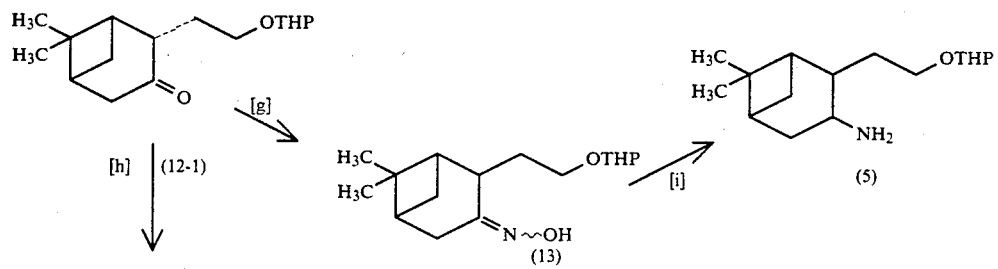

-continued
Scheme [B]

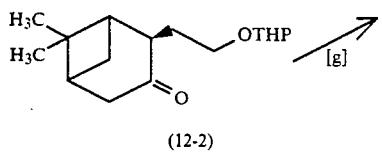
(12-2)

Explaining each step briefly, step [g] is the reaction to form oxime. It may be carried out by reacting with using a hydroxylamine hydrochloride, in the presence of barium carbonate, in an inert organic solvent (lower alkanol etc.) at from a room temperature to a refluxing temperature.

Step [h] is inversion. It may be carried out by refluxing with using a base (potassium tert-butoxide etc.), in an inert organic solvent (tetrahydrofuran, lower alkanol etc.).

Step [i] may be carried out by reducing the compound of the formula (13) with using Raney Nickel as catalyst, or refluxing with using metallic sodium in an lower alkanol (propanol etc.).

The compound of the formula (12-1) may be prepared with using β-pinene, α-pinene and 2-oxonorpinane as starting material by the same process as described in the specification of Japanese Patent Kokai No. 61-49.

The compounds of the formula (V), (VI) and (VII) wherein

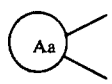

represents the groups of the formula (Aa-1), (Aa-3), (Aa-4), (Aa-6) and (Aa-7) may be prepared, for example, as follows. In scheme, $R^{51}$ represents a phenyl group substituted or unsubstituted, or lower alkyl group. The other symbols represent the same meaning as defined hereinbefore.

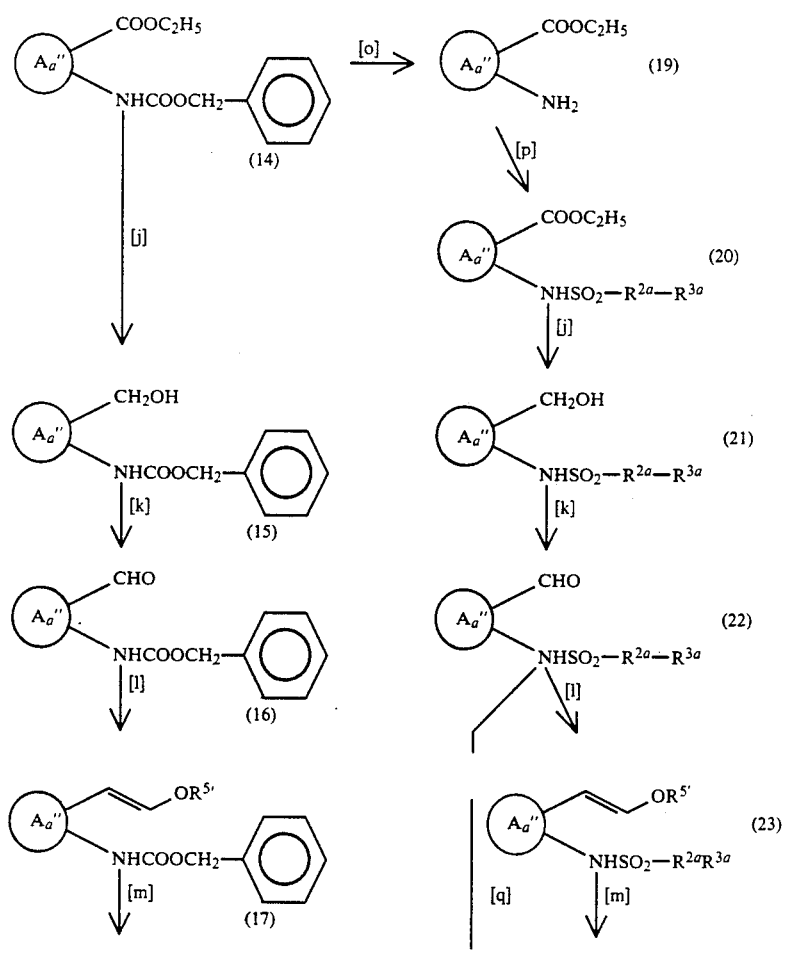

Scheme [C]

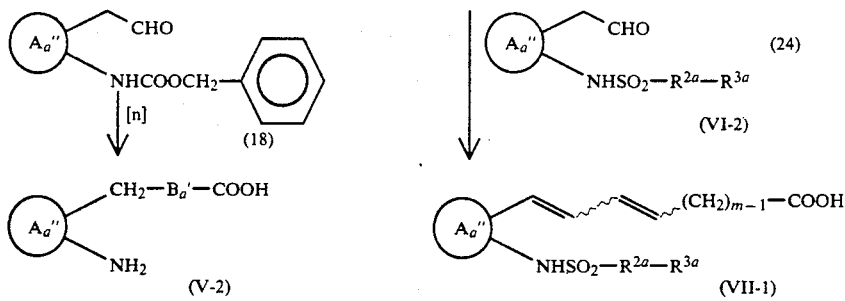

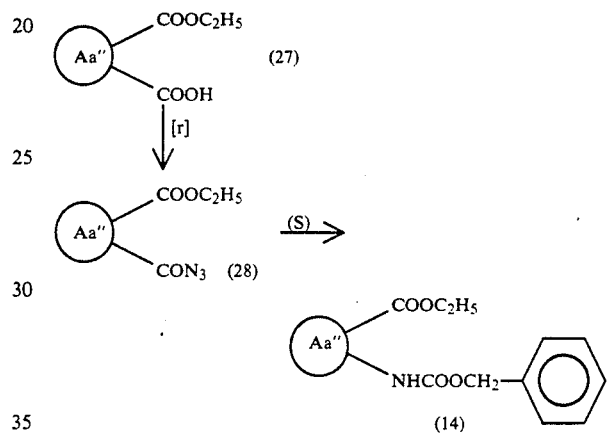

Explaining each step briefly, step [j] is reduction. It may be carried out with using lithium aluminum hydride or diisobutyl aluminum hydride, in an inert organic solvent (tetrahydrofuran, diethylether, lower alkanol etc.), at from $-78°$ C. to a room temperature.

Step [k] is oxidation. It may be carried out by the same procedure as step [c] described hereinbefore.

Step [l] is Wittig's reaction. It may be carried out with using the compound of the general formula:

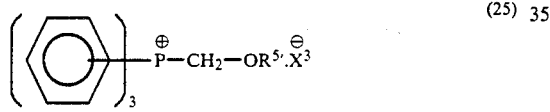

(wherein, $R^{51}$ represents the same meaning defined hereinbefore, $X^3$ represents a halogen atom.), under the same condition as step [d] described hereinbefore.

Step [m] is hydrolysis. It may be carried out by reacting with using an acid (hydrochloric acid, acetic acid, oxalic acid etc.), in an inert organic solvent (THF, dioxane, lower alkanol etc.), at a temperature of from $50°$ C. to $100°$ C.

Step [n] may be carried out by the same procedure as from step [d] to [e].

Step [o] is elimination of a benzyloxycarbonyl group. It may be carried out by the same reduction as step 4 described hereinbefore.

Step [p] is sulfonylation. It may be carried out by the same procedure as step 1 described hereinbefore.

Step [q] is Wittig's reaction. It may be carried out with using the compound of the general formula:

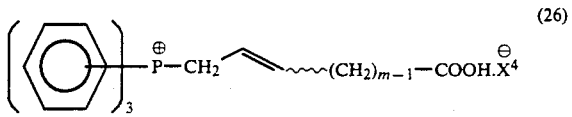

(wherein $X^4$ represents a halogen atom, m represents the same meaning as described hereinbefore.) under the same condition as step [d] described hereinbefore.

The compound of the formula (14) may be prepared as follows.

Explaining each step briefly, step [r] may be carried out by reacting with using an ethyl chloroformate, in the presence of a tertiary amine (triethylamine etc.), in an inert organic solvent (acetone etc.), at from $31$ $10°$ C. to a room temperature, when adding sodium azide and reacting at the same temperature as above.

Step [s] may be carried out by refluxing the compound of the formula (28) in an inert organic solvent (toluene etc.) to obtain the corresponding isocyanate and then reacting it and benzyl alcohol in the presence of a tertiary amine (triethylamine etc.) or an acid (p-toluenesulfonic acid etc.).

The compound of the formula (27) used as starting material may be prepared by (1) refluxing the corresponding acid anhydride in ethanol, (2) hydrolyzing the corresponding diethyl ester by one equivalent of alkali or (3) hydrolyzing the corresponding diethyl ester with using a hydrolytic enzyme.

Acid anhydrides and diethyl esters corresponding to the compound of the formula (27) are known as ($\pm$) bodies or may be prepared easily from known dicarboxylic acids.

If desired, ($\pm$) bodies may be resolved in each optically active compound. The optical resolution may be carried out by the known method [See Tables of resolving agents and optical resolutions, University of Hotre dame press (1972) etc.] in a preferable step, for example, step of the compound (27).

Optical active compounds of the compounds of the general formula (I), wherein

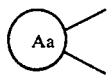

represents a group of the formula (Aa-1), (Aa-3), (Aa-4) or (Aa-6) and which have such a configuration that the upper chain (—CH$_2$—Ba—R$^1$) and the lower chain (—NHSO$_2$—R$^{2a}$—R$^{3a}$) bond in trans against the ring with respect to each other, may be prepared as follows: 1,3-cyclopentadiene, 1,3-cyclohexadiene, furan or butadiene are reacted with dimenthyl fumarate or menthylmandelyl fumarate in the presence of Lewis' acid. The optically active Diels-Alder adduct thus obtained may be converted into a monomenthylester carboxylic acid or the other monoalkylester carboxylic acid, corresponding to the compound of the formula (27) and subject to subsequent reactions. On this occasion, a double bond in the Diels - Alder adduct must be reduced in a suitable step [for example, the Diels-Alder adduct or the compound of the formula (19)].

The compounds of the general formula (IIa), (IIb) and (IIc), used as starting materials may be easily prepared by methods known per se. For example, the compound of the formula (IIa) may be prepared according to the following Scheme A'.

In the scheme, R$^2$ represents an alkyl group of from 1 to 4 carbon atom(s), R$^3$ represents a methanesulfonyl group (referred to as Ms hereafter) or a p-toluenesulfonyl group (referred to as Ts hereafter) and the other symbols represent the same meaning as defined hereinbefore.

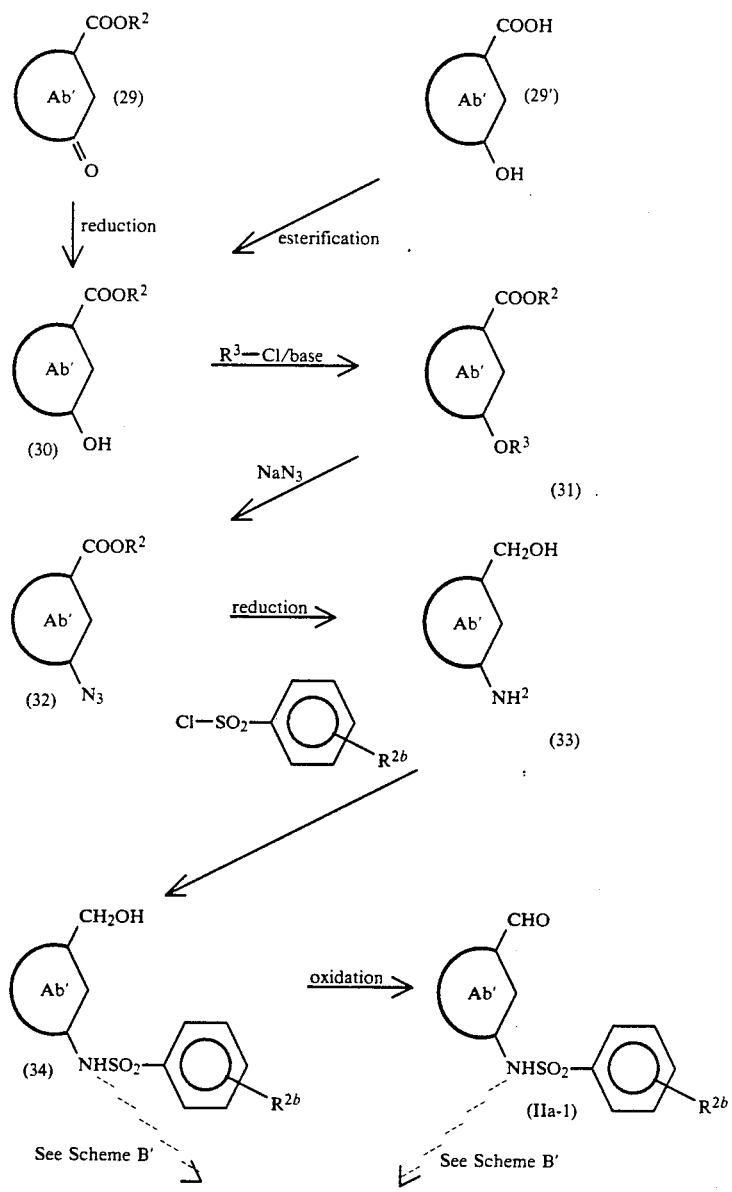

Scheme A'

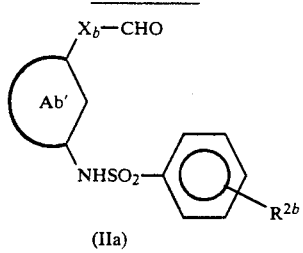

(IIa)

In scheme A', each step is well known to those skilled in the art. Furthermore, the process for the preparation of the compound of the formula (IIa) from the compound of the formula (34) or from that of the formula (IIa-1) may be depicted in the following Scheme B'. Wherein

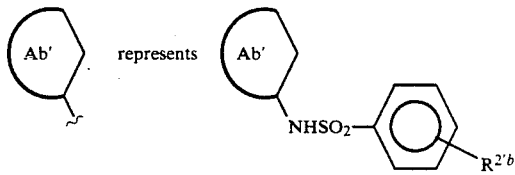

$R^4$ represents an alkyl group of from 1 to 4 carbon atom(s), $\Phi$ represents a phenyl group and the other symbols represents the same meaning as defined hereinbefore.

Scheme B'

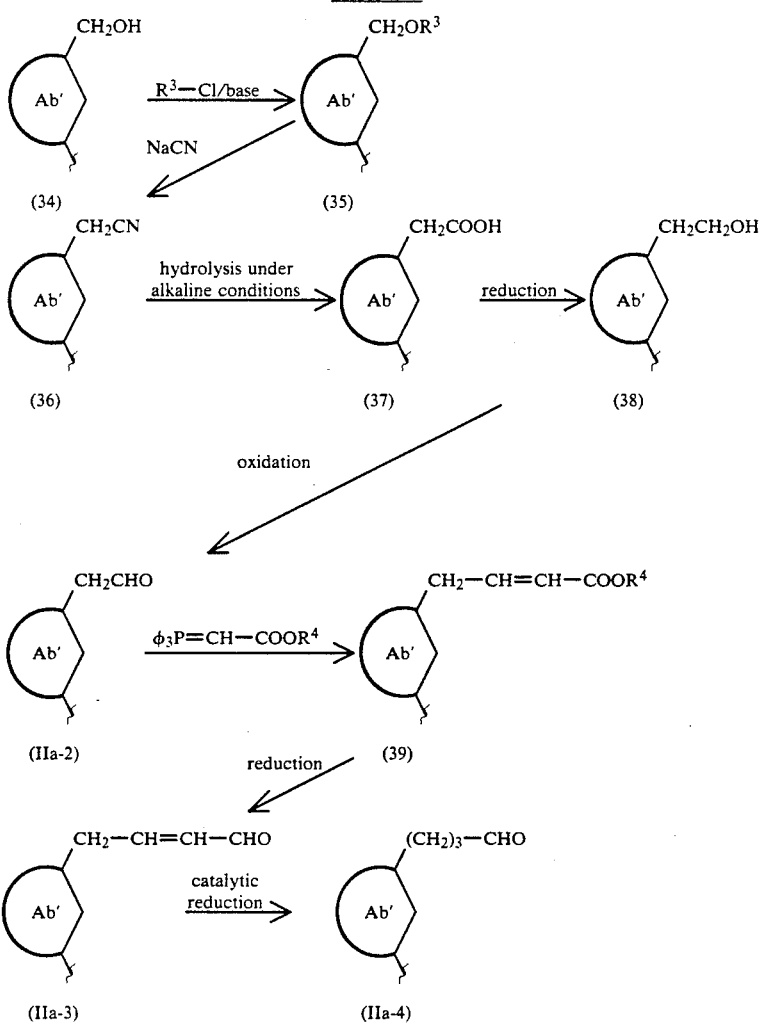

-continued
Scheme B'
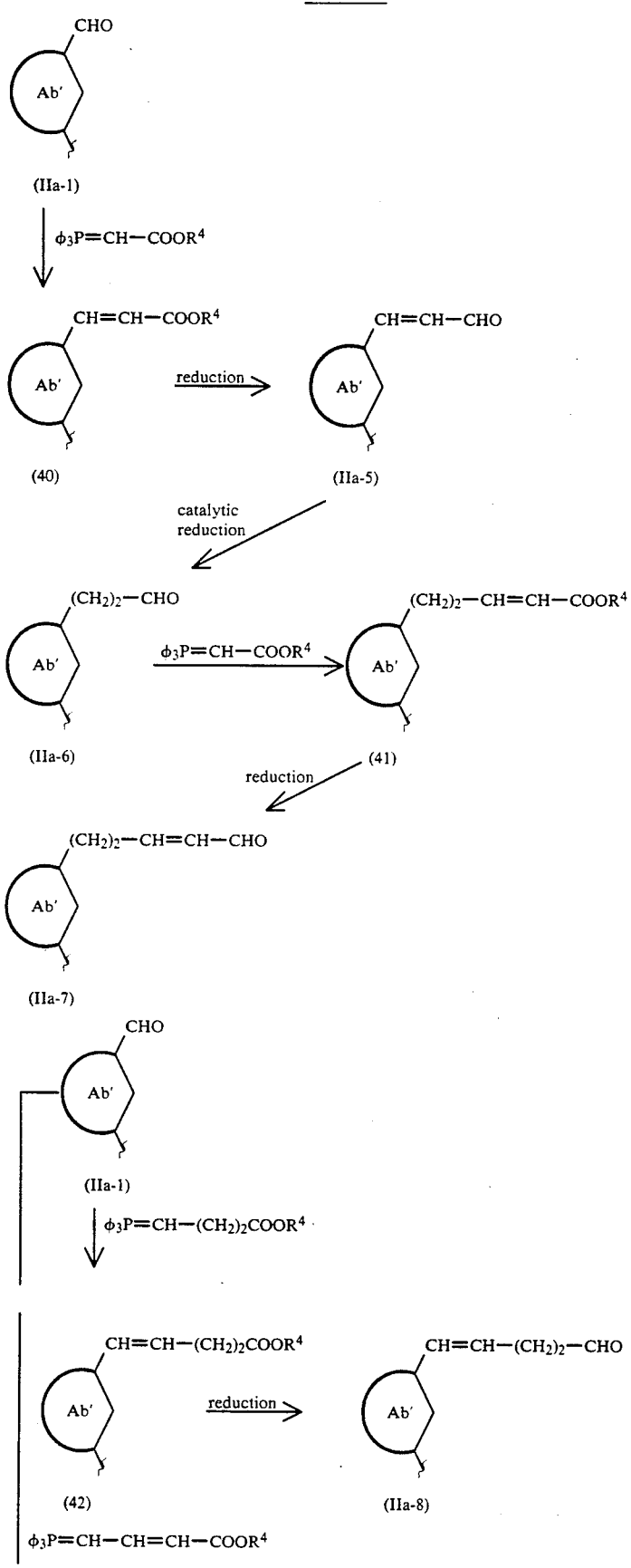

Scheme B'

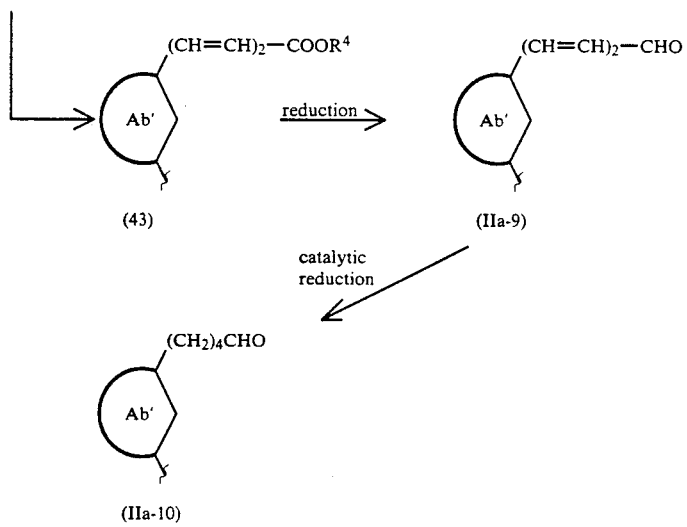

Scheme B', each step is well known to those skilled in the art. The compound of the general formula (IIa) wherein $X_b$ represents a branched-chain alkylene group or alkenylene group, may also be prepared by the same methods as depicted in Scheme B' or by the combination of known methods.

On the other hand, the compounds of the general formulae (IIb) and (IIc), used as other starting materials, may be easily prepared by methods known per se. For example, these compounds may be prepared according to the following Scheme C'.

In the scheme, $R^s$ represents a trialkylsilyl group, $R^6$ represents an alkyl group of from 1 to 4 carbon atom(s), THP represents tetrahydropyran-2-yl group and the other symbols represents the same meaning as defined hereinbefore.

Scheme C'

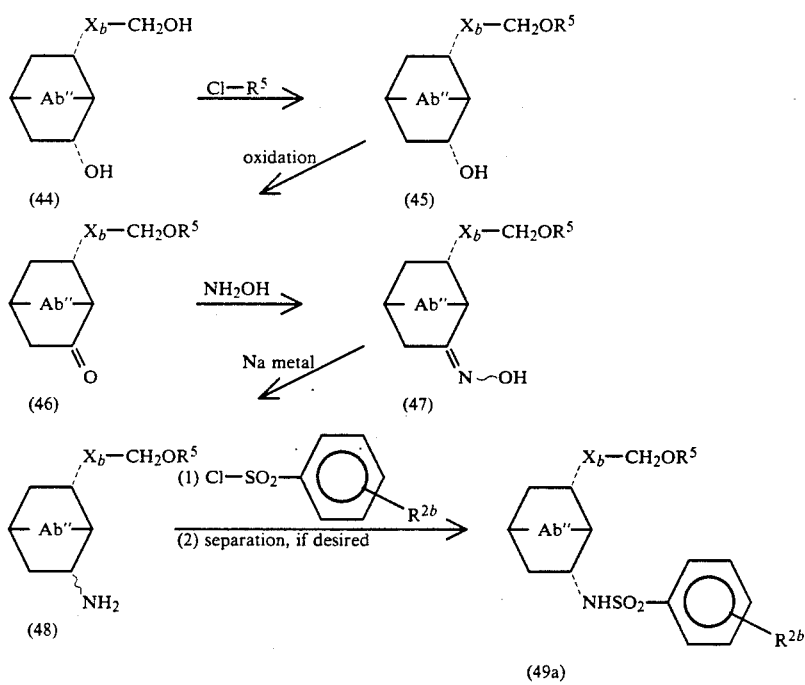

+

Scheme C'
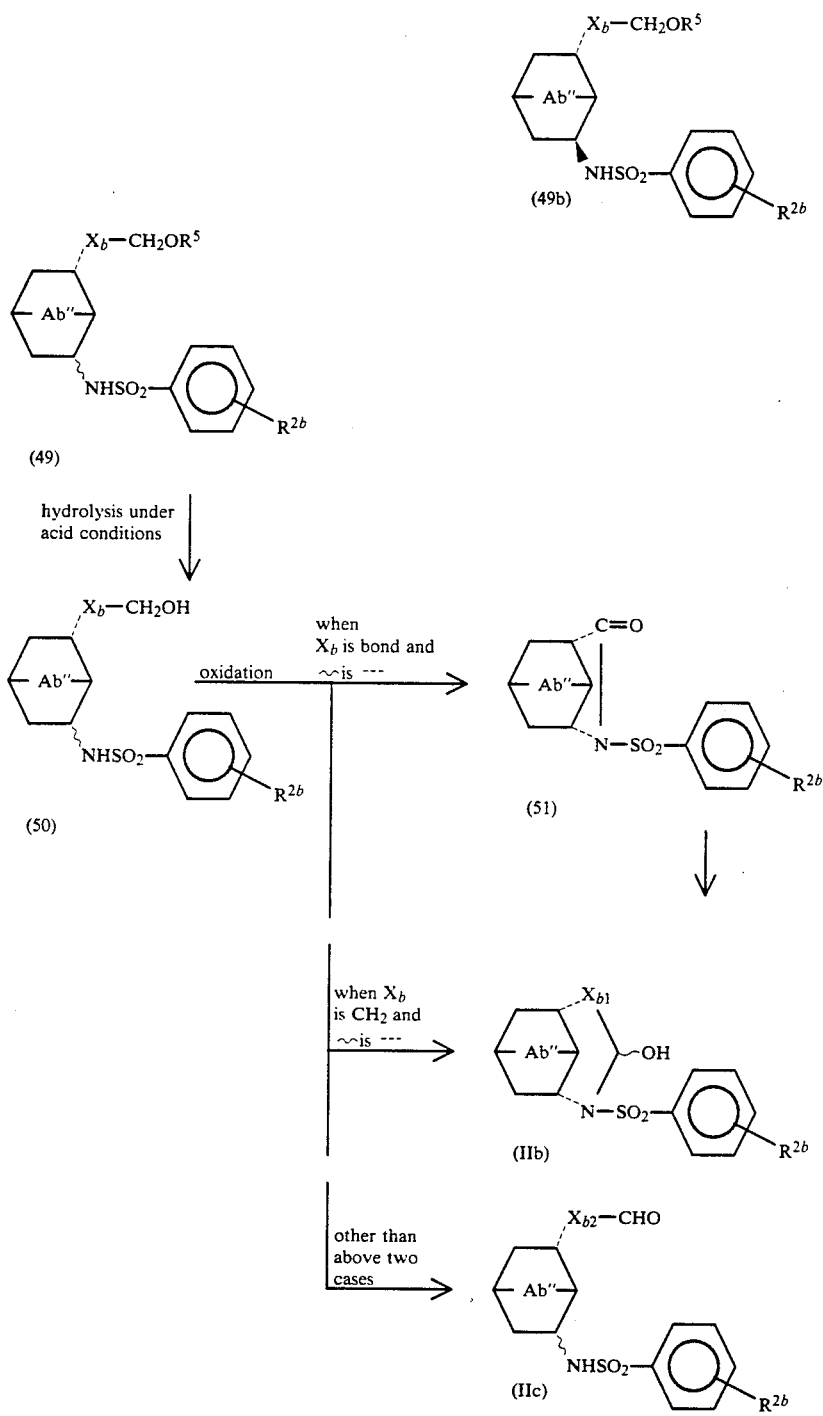
In Scheme C', each step is well known to those skilled in the art.
The starting material in the scheme, i.e. the compound of the formula (44), may be easily prepared by methods known per se. For example, the compounds may be prepared according to the following Scheme D' and E', wherein the various symbols represents the same meaning as defined hereinbefore.

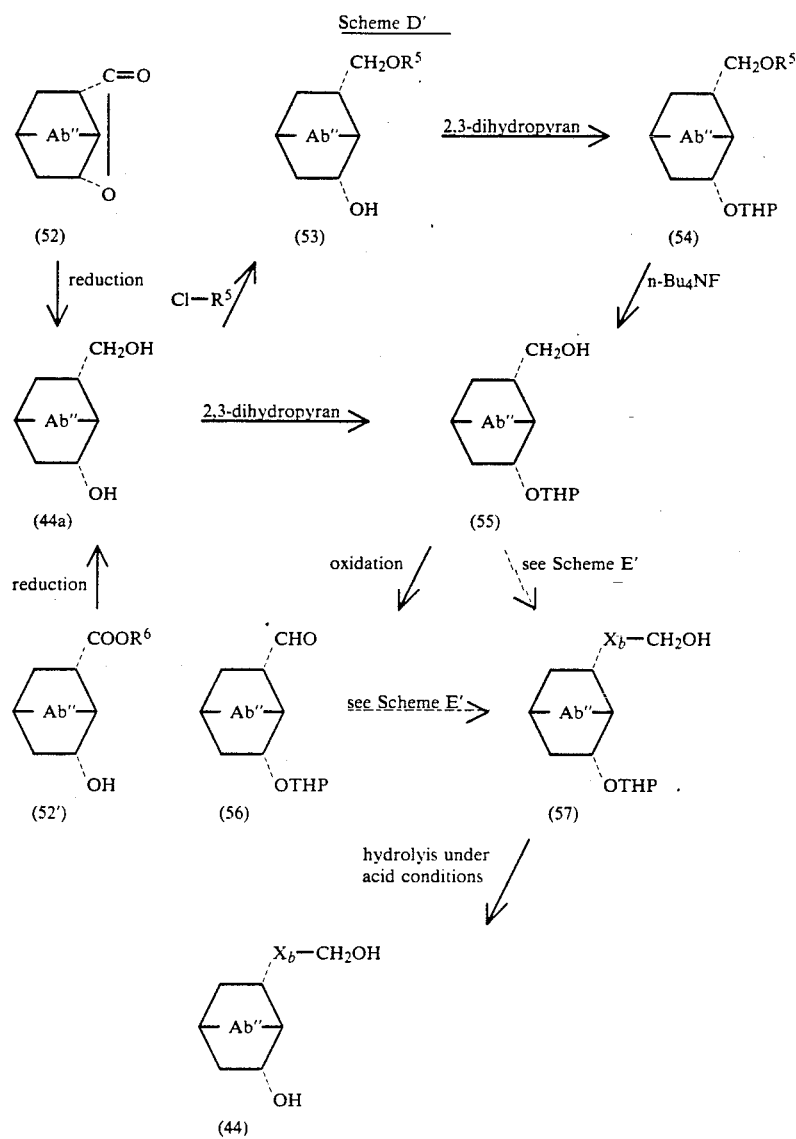
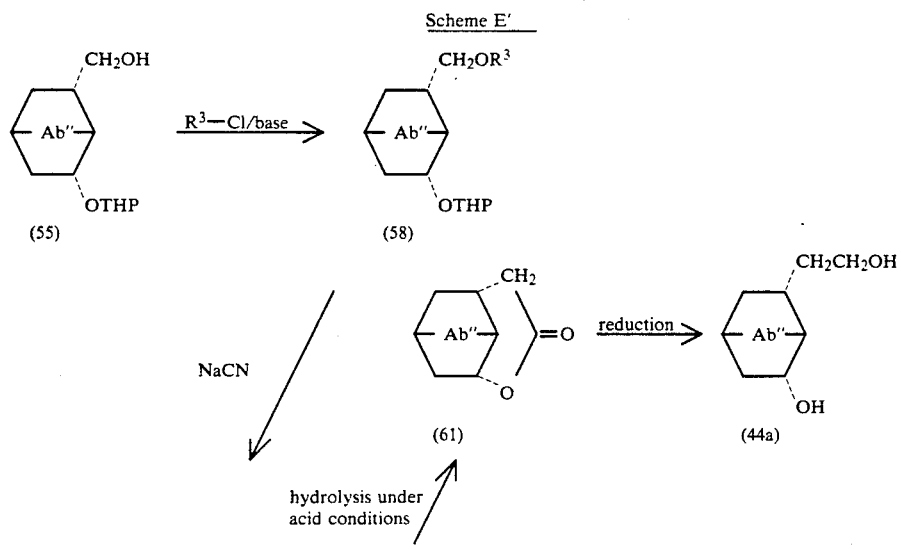

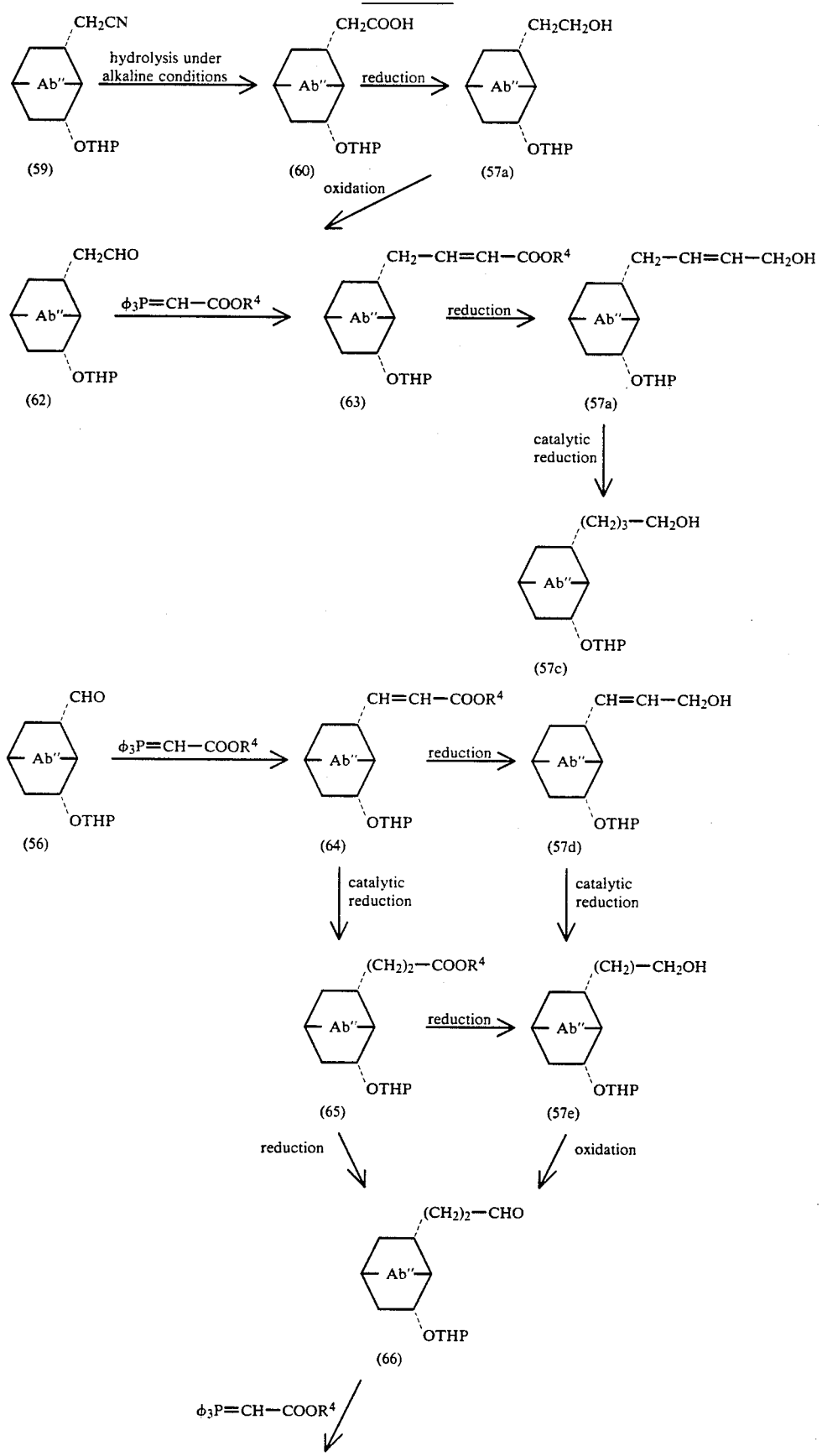

-continued
Scheme E'

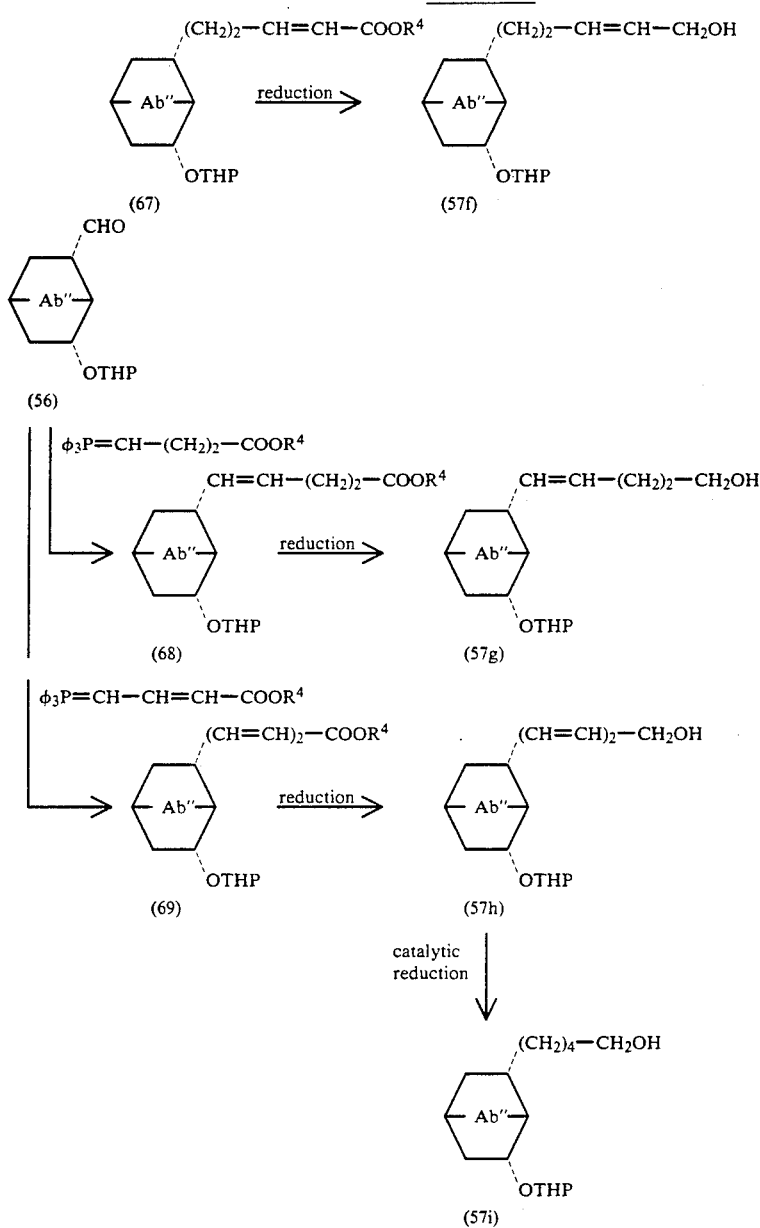

In the above schemes, each step is well known to those skilled in the art. In Scheme E', the compound of the general formula (57) wherein $X_b$ represents a branched-chain alkylene group or alkenylene group, may also be prepared by the same methods as depicted in Scheme E' or by the combination of known methods.

The compounds of the general formulae (IIb) and (IIc), having other stereo-configuration, may be prepared from the corresponding starting materials by the same methods as depicted in the above schemes.

The starting materials of the formula (29), (29'), (30), (31), (42) and (42'), and further the compounds corresponding to those of the formula (42) and (42'), having other stereo-configuration, are well known per se or may be easily prepared from known compounds by methods known per se.

For example, the compounds of the formulae (30) and (31) wherein

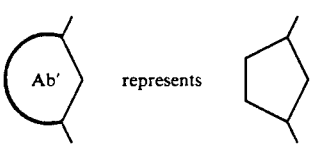 represents are described in the specification of the Japanese Patent Kokai No. 61-103850, the European Patent Publication No. 181100 and the U.S. Pat. No. 4640931, and the compound of the formula (29') wherein

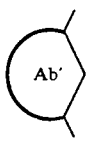

represents (±)

is described in J. Am. Chem. Soc., 74, 5912 (1952). The compound of the formula (52) wherein

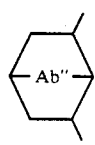

represents (±)

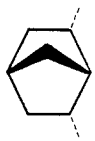

is described in Tetrahedron, 35,2225 (1979) and the compound of the formula (52') wherein

represents (±)

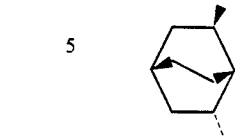

and that of the formula (52) wherein

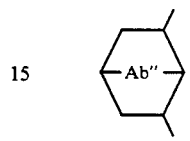

represents (±)

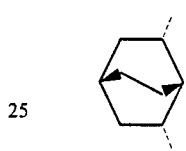

are described in Helv. Chim. Acta, 67, 1859 (1984).

If desired, (±) bodies may be resolved into each optically active compound. The optical resolution may be carried out by the known method [See Tables of resolving agents and optical resolutions, University of Hotre dame apress (1972) etc.] in a preferable step.

In the said starting materials, compounds of the general formulae (IId) and (IIIa) may be prepared according to the following Scheme A" and B". Various symbols in Scheme A" and B" are defined hereinafter or are the same meaning as defined hereinbefore;

Ts: a tosyl group.

Each steps in Scheme A" and B" may be carried out by known methods hereinbefore described by using appropriate reagents.

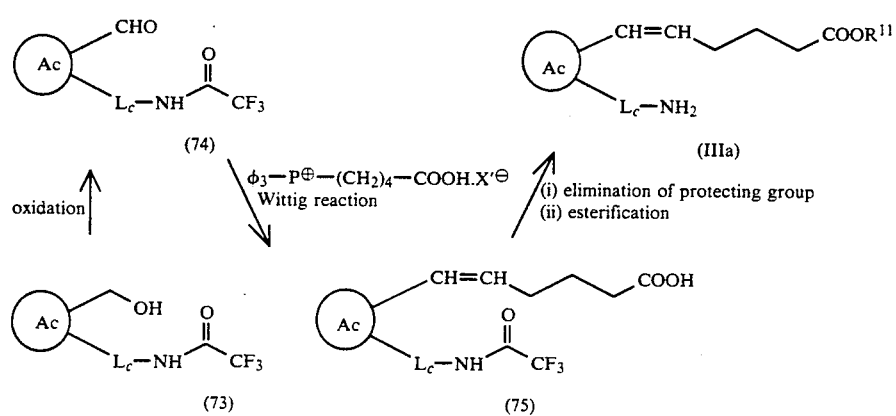

-continued
Scheme A"
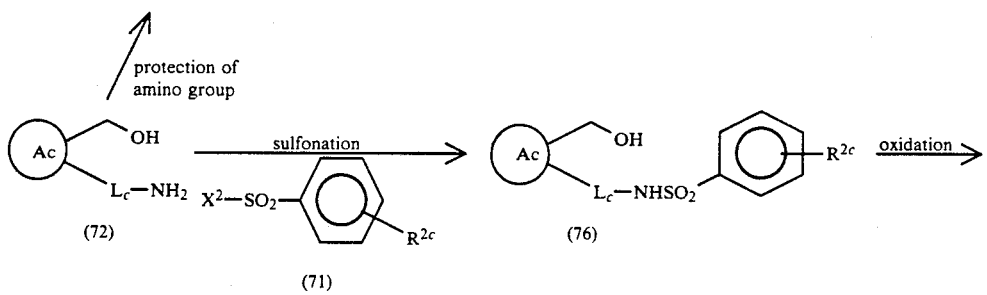
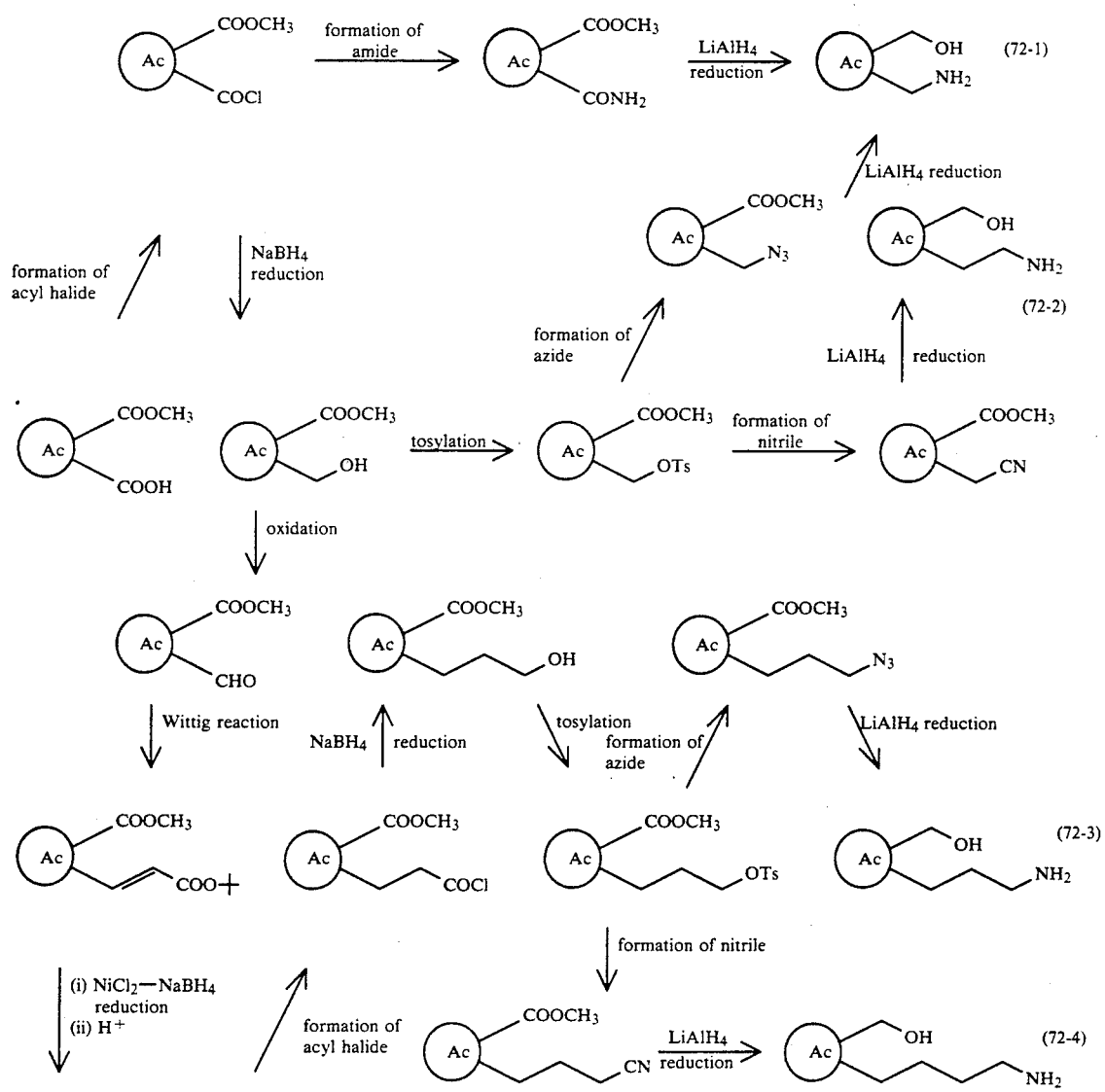

-continued
Scheme B"

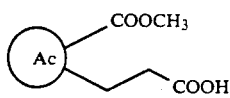

Starting materials and reagents, used in the present invention are known per se or may be prepared by methods known per se.

Throughout the specification in each reaction, products may be purified by conventional methods, for example, distillation at atmospheric or reduced pressure, high performance liquid chromatography, thin layer chromatography or column chromatography using silica gel or magnesium silicate or washing or recrystallization. Purification may be carried out after each reactions or a series of reactions.

[Cyclodextrin clathrates and salts]

The cyclodextrin clathrates of carbocyclic sulfonamide derivatives shown by the general formula (I) may be prepared with using α-, β- or γ- cyclodextrin or a mixture thereof, by the method described in the specification of Japanese Patent Kokoku Nos. 50-3362 or 52-31404 and British Patent No. 1351238 and U.S. Pat. No. 3816393.

The stabilities of the compounds shown by the general formula (I) are enlarged by converting them into cyclodextrin clathrates.

The acid of the general formula (I) wherein $R^{11}$ represents a hydrogen atom are converted into salts by known methods.

The slats are preferably non-toxic ones. The non-toxic salts herein referred mean salts of cations such that they are relatively innocuous to living body (animals including humans) tissues and that the effective pharmacological properties of the compound(s) of the general formula (I) are not impaired by side effect(s) resulting from the cations when used in an amount required for the treatment.

And water-soluble salts are preferable.

Suitable salts include, for example, a salt of an alkali metal (sodium, potassium etc.), a salt of an alkaline earth metal (calcium, magnesium etc.), an ammonium salt and a pharmaceutically acceptable (non-toxic) amine salt.

Amines suitable for forming such salts with carboxylic acid are well known, and include, for example, those amines which are theoretically obtained by substituting one or more of hydrogen atom(s) of ammonia by other groups.

Examples of such amine are, an amino acid (arginine, lysine, glutamine, histidine, asparagine etc), a sugar-amine (N-methylglucane, N-methylmannosamine, N-methylgalactosamine, N-methylfructosamine, N-methylarabinosamine, N-methylribosamine, N-methyllactosamine etc.) and another amine (ethanolamine, triethanolamine, triethylamine, meglumine, guanidine etc.).

The salt an be obtained by known method per se, for example, by reacting an acid of the general formula (I) wherein $R^{11}$ represents a hydrogen atom with a suitable base (e.g. a hydroxide or carbonate of an alkali metal or an alkaline earth metal, ammonia or an amine) in theoretical amounts in an appropriate solvent.

The slat can be isolated by freeze-drying the solution, or by filtration if the salt is sufficiently insoluble to the reaction solution, or if necessary, by removing part of the solvent followed by filtration.

[Pharmacological Activities of the compounds of the present invention]

The compounds of the general formula (I), of the present invention, possess an antagonistic action against thromboxane $A_2$, especially inhibitory effect on platelet aggregation, on contraction of smooth muscle or an increasing of blood pressure.

For example, in a standard laboratory test, the effects were possible to be confirmed by (i) inhibitory effect on platelet aggregation induced by $STA_2$ (9α,11α-epithio-15α-hydroxy-11α-carbathromba-5Z,13E-dienoic acid) in human blood, (ii) inhibitory effect on contraction of smooth muscle induced by $STA_2$ in guinea pigs or (iii) inhibitory effect on increasing of blood pressure induced by $STA_2$ in guinea pigs (intravenously and orally).

The results about a part of experiments carried out are shown in the following table 1.

TABLE I

Inhibitory effects on platelet aggregation induced by $STA_2$ in human blood

| Example No. of compounds | Structure | Inhibitory effects on platelet aggregation ($IC_{50}$, M) |
|---|---|---|
| 1 (i) | 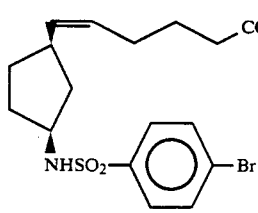 | $3.0 \times 10^{-8}$ |

TABLE I-continued

Inhibitory effects on platelet aggregation induced by $STA_2$ in human blood

| Example No. of compounds | Structure | Inhibitory effects on platelet aggregation ($IC_{50}$, M) |
|---|---|---|
| 1 (m) | 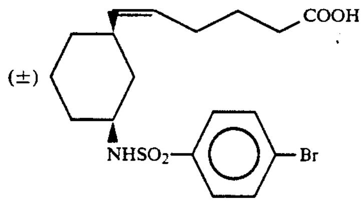 | $1.7 \times 10^{-7}$ |
| 1 (c) | 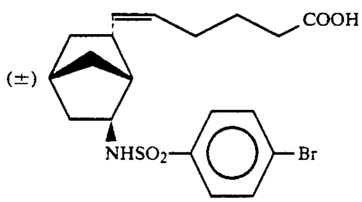 | $1.0 \times 10^{-6}$ |
| 4 (a) | 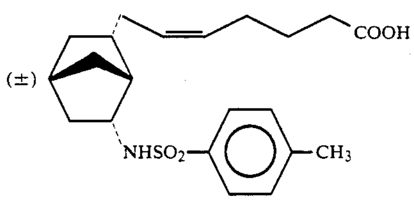 | $1.78 \times 10^{-6}$ |
| 1 (a) | 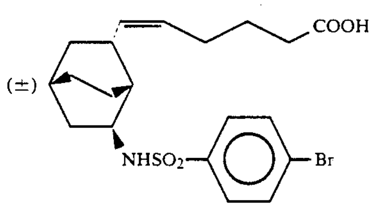 | $6.6 \times 10^{-7}$ |
| 1 (r) | 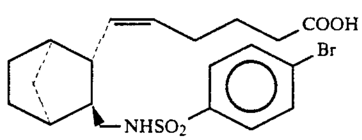 | $2.8 \times 10^{-7}$ |
| 1 (p) | 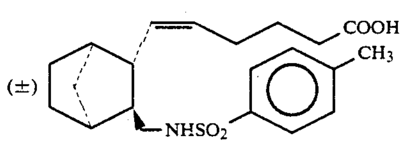 | $9.0 \times 10^{-8}$ |
| 1 (q) | 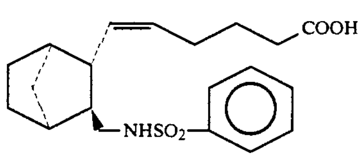 | $1.67 \times 10^{-6}$ |
| 1 (s) | 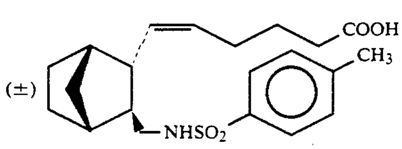 | $5.2 \times 10^{-7}$ |

TABLE I-continued

Inhibitory effects on platelet aggregation induced by $STA_2$ in human blood

| Example No. of compounds | Structure | Inhibitory effects on platelet aggregation ($IC_{50}$, M) |
|---|---|---|
| 1 (t) | (±) cyclohexyl-CH=CH-CH2-CH(COOH)-C6H4-Br, with NHSO2 | $5.2 \times 10^{-7}$ |
| 1 (u) | norbornyl-CH=CH-CH2-CH(COOH)-C6H4-Br, with CH2-NHSO2 | $1.0 \times 10^{-6}$ |
| 1 (v) | (±) cyclopentyl-CH=CH-CH2-CH(COOH)-C6H4-Br, with NHSO2 | $2.2 \times 10^{-7}$ |
| 1 (w) | (±) cyclopentyl-CH=CH-CH2-CH(COOH)-C6H4-CH3, with NHSO2 | $6.8 \times 10^{-7}$ |
| 1 (x) | norbornyl-CH=CH-CH2-CH(COOH)-C6H4-CH3, with NHSO2 | $5.0 \times 10^{-8}$ |
| 1 (y) | norbornyl-CH=CH-CH2-CH(COOH)-C6H4-Br, with NHSO2 | $1.0 \times 10^{-8}$ |

The methods for the experiments hereinbefore described are detailed as follows.

(i) Inhibitory effect on platelet aggregation induced by $STA_2$ in human blood: Whole blood of healthy male human adult was collected with citric acid, and the mixture (20 ml) was centrifuged (180×g) for 10 min. The supernatant obtained was diluted with sufficient platelet poor plasma to obtain plasma which contains 300,000 platelet cells power μl. A solution of tested compound in ethanol (1 μl) was added to the obtained plasma (250 μl), and then a solution of $STA_2$ is ethanol was added to the mixtures. The measurement was carried out followed by the method of Born and then $IC_{50}$ was calculated.

(iii) Inhibitory effect on increasing of blood pressure induced by $STA_2$ in guinea pigs: A 7% sodium bicarbonate buffer solution (pH 7.6–8.6) of each tested compounds was administered intravenously via carotid vein or orally to a urethane-anaesthetized male guinea pig weighing 250~350 g, at a rate of 10-1000 μg/kg animal body weight. And then guinea pigs were administered intravenously a solution of $STA_2$ in phosphate buffer (pH 7.4). change of the blood pressure was measured at carotid artery and then inhibition ratio (%) was calculated.

Of the compounds of the general formula (I) of the present invention, some compounds have an antagonistic effect on thromboxane $A_2$, especially inhibitory effect on increasing of blood pressure, lasting for a long time, and have a weak agnostic effect on thromboxane $A_2$ (stimulatory effect on increasing of blood pressure).

For example, in a standard laboratory test, the effects were possible to be confirmed by (i) inhibitory effect on increasing of blood pressure induced by $STA_2$ in guinea pigs (antagonistic effect) and (ii) stimulatory effect on increasing of blood pressure in guinea pigs (agnostic effect).

The results about a part of experiments carried out are shown in the following Table II and FIGS. 1, 2 and 3.

TABLE II (i) Inhibitory effects on increasing of blood pressure induced by $STA_2$ in guinea pigs and
(ii) Stimulatory effect on increasing of blood pressure in guinea pigs

| Example No. of compounds | Structure | (i) Duration of more than 50% inhibit on increasing of blood pressure induced by $STA_2$ in guinea pig (min) 100 μg/kg, p.o. | (ii) Effect of increasing of blood pressure in guinea pig (mmHg) 100 μg/kg, i.v. (n = 2~4) |
|---|---|---|---|
| The compounds of the present invention | | | |
| 6 | 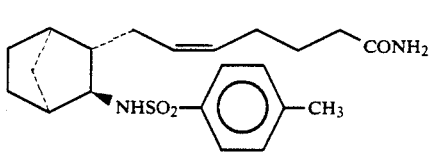 | >340 | 9 |
| 7 | 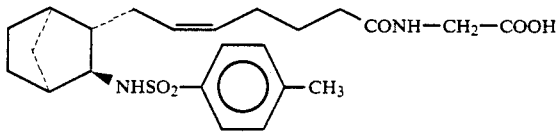 | >270 | 9 |
| 7 (b) | 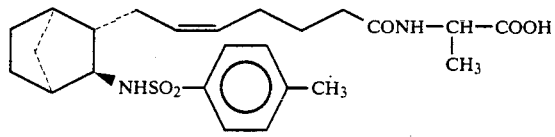 | >290 | 11 |
| 7 (c) | 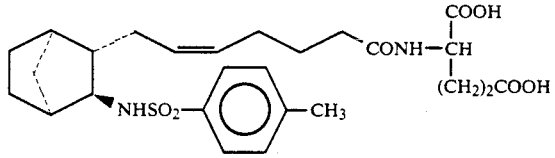 | >290 | 7 |
| 8 | 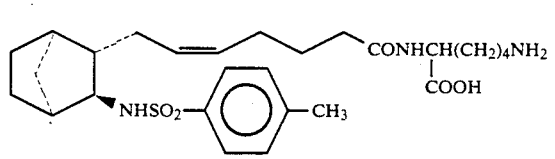 | 305 | 7 |
| 5 (g) | 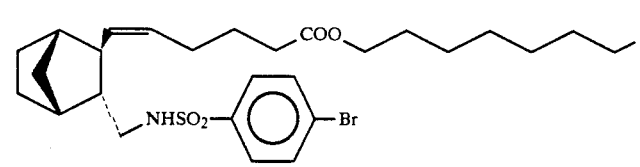 | >300 | 1 |
| 5 (h) | 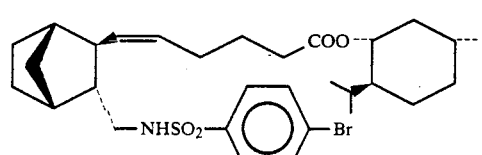 | >300 | 1 |
| 6 (d) | 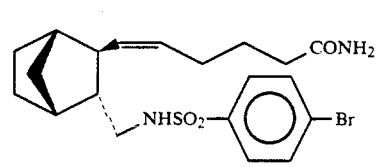 | >240 | 6 |

TABLE II-continued (i) Inhibitory effects on increasing of blood pressure induced by $STA_2$ in guinea pigs and
(ii) Stimulatory effect on increasing of blood pressure in guinea pigs

| Example No. of compounds | Structure | (i) Duration of more than 50% inhibit on increasing of blood pressure induced by $STA_2$ in guinea pig (min) 100 μg/kg, p.o. | (ii) Effect of increasing of blood pressure in guinea pig (mmHg) 100 μg/kg, i.v. (n = 2~4) |
|---|---|---|---|
| The compared compound | (structure with cyclohexane, NHSO₂-phenyl-CH₃, and COOH chain) | 205 | 36 |

The compared compound:
The optically active compound of the compound (compound No. 26) described in the specification of British Patent Kokai No. 2184118. (Configuration: 1R, 2S, 3S, 4S)

The methods for the experiments described in Table II and FIGS. 1, 2 and 3 are detailed as follows.

Inhibitory effect on increasing of blood pressure induced by $TXA_2$ in guinea pigs and stimulatory effect on increasing of blood pressure in guinea pigs: A 7% sodium bicarbonate buffer solution (pH 7.6~8.6) of each tested compounds was administered intravenously via carotid vein or orally to a urethane-anaesthetized male guinea pig weighing 250~350 g, at a rate of 100 μg/kg animal body weight. Increasing of blood pressure was measured in guinea pigs administered test compounds intravenously. On the other hand, to guinea pigs administered test compounds orally, then a solution of $STA_2$ in phosphate buffer (pH 7.4) was administered. Change of the blood pressure was measured at carotid artery and then inhibition ratio (%) was calculated.

The foregoing results show that the compounds of the present invention possess an antagonistic effect on $TXA_2$. Some of them have an antagonistic effect on $TXA_2$, especially inhibitory effect on increasing of blood pressure, lasting for longer time than the compared compounds, and have a weak agnostic effect on $TXA_2$, i.e. stimulatory effect on increasing of blood pressure.

[Application for pharmaceuticals]

The compounds of the present invention, of the general formula (I), cyclodextrin clathrates thereof and non-toxic salts thereof have an antagonistic effect on $TXA_2$ such as an inhibitory effect on platelet aggregation, on contraction of smooth muscle or on increasing of blood pressure, and are, therefore, useful for prevention and/or treatment of inflammation, hypertension, thrombus, cerebralapoplexy, asthma, cardiac infarction, angina pectoris, cerebral infarction and death by acute cardiac disorders in mammals, in particular in humans, which are considered to be induced by thromboxane $A_2$.

For the purpose hereinbefore described, the compounds of the present invention, of the general formula (I), cyclodextrin clathrates thereof and non-toxic salts thereof may normally be administered systemically or partially; usually by oral or parenteral administration. The doses to be administered are determined depending upon age, body weight, symptom, the desired therapeutic effect, the route of administration, and the duration of the treatment etc. In the human adult, the doses per person per does are generally between 1 mg and 5 g, by oral administration up to several time per day, and between 10 μg and 1 g, by parenteral administration up to several times per day. As mentioned above the doses to be used depend upon various conditions. Therefore, there are cases in which doses lower than or greater than the ranges specified above may be used.

Solid compositions according to the present invention for oral administration include compressed tablets, dispersible powders and granules. In such solid compositions, one or more of the active compound(s) is or are, admixed with at least one inert diluent such as lactose, mannitol, glucose, hydroxypropylcellulose, microcrystalline cellulose, starch, polyvinylpyrrolidone or magnesium metasilicate aluminate. The compositions may also comprise, as is normal practice, additional substances other than inert diluents e.g. lubricating agents such as magnesium stearate, disintegrating agents such as cellulose calcium glycolate, stabilizing agent e.g. lactose and assistant for dissolving e.g. arginine, glutamic acid or aspartic acid. The tablets or pills may, if desired, by made into gastric film-coated or enteric film-coated tablets or pills, such as sugar-coated, gelatin-coated, hydroxypropyl cellulose-coated or hydroxypropylmethyl cellulose phthalate-coated tablets or pills; two or more of layers may be used. The compositions for oral administration also include capsules of absorbable material such as gelatin.

Liquid compositions for oral administration include pharmaceutically-acceptable emulsions, solutions, suspensions, syrups and elixirs containing inert diluents commonly used in the art such as distilled water or ethanol. Besides inert diluents such compositions may also comprise adjuvants such as wetting and suspending agents, and sweetening, flavouring, perfuming and preserving agents.

Other compositions for oral administration include spray compositions which may be prepared by known methods and which comprise one or more of the active compound(s).

Preparations for injection according to the present invention for parenteral administration include sterile aqueous or non-aqueous solutions, suspensions or emulsions, Examples of aqueous solvents or suspending media are distilled water for injection and physiological salt solution. Examples of non-aqueous solvents or suspending media are propylene glycol, polyethylene glycol, vegetable oils such as olive oil, alcohols such as ethanol, POLYSORBATE 80 (registered Trade Mark). These compositions may also include adjuvants such as preserving, wetting, emulsifying, dispersing agents, stabilizing agents (e.g. lactose) and assistant agents for dissolving (e.g. arginine, glutamic acid or aspartic acid).

They may also be manufactured in the form of sterile solid compositions which can be dissolved in sterile water or some other sterile injectable medium immediately before use.

Other compositions for parenteral administration include liquids for external use, and endermic liniments such as ointments, suppositories for rectal administration and pessaries for vaginal administration which comprise one or more of the active compound(s) and may be prepared by known methods.

The following reference examples and examples illustrate the present invention, but not limit the present invention.

In the reference examples and examples, "bp", "mp", "TLC", "NMR", "IR" and "MS" represent "boiling point", "melting point", "Thin layer chromatography", "Nuclear magnetic resonance spectrum", "Infrared absorption spectrum" and "Mass spectrum", respectively.

The solvents in the parentheses show the developing or eluting solvents and the rations of the solvents used are by volume in chromatographic separations.

Unless otherwise specified, "NMR" was measured in a chloroform-d (CDCl$_3$) solution and "IR" was measured by the liquid film method respectively.

In the structural formulae, cbz means benzyloxycarbonyl group, Menth means menthyl group, tosyl group means (4-methylphenyl)-sulfonyl group, mesyl group means methanesulfonyl group, BMS means tert-butyldimethylsilyl group and THP means tetrahydropyran-2-yl group.

And (±) in reference examples and examples represent the mixture of enantimers having different angels of rotation as generally used in the nomenclature. For example (±),

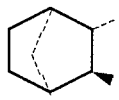

represents the mixture of

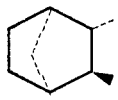 and  , and * are added to indications of absolute configuration at the same time.

Reference Example 1

(3-aminocyclopentyl)emthanol

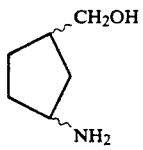

(1) Synthesis of tert-butyl 3-mesyloxycyclopentanoate

Mesyl chloride (0.15 ml) was added dropwise to tert-butyl 3-hydroxycyclopentanoate (373 mg) dissolved in methylene chloride (2 ml) and pyridine (0.32 ml) at a temperature of 0° C. The mixture was stirred at a room temperature for 4 hours. The reaction mixture was poured into ice-water (10 ml). The mixture was extracted with ethyl acetate. The extract was washed with water, dried over magnesium sulfate and then evaporated to obtained the title compound having the following physical data.

TLC(n-hexane:ethyl acetate=1:2): Rf 0.54.

(2) Synthesis of tert-butyl 3-azidocyclopentanoate

Sodium azide (156 mg) was added to the mesylate [prepared in (1)]dissolved in hexamethylphosphamide (3 ml). The mixture was poured into water. The mixture was extracted with ethyl acetate. The extract was washed with water, dried over magnesium sulfate and then evaporated to obtain the title cohpound having the following physical data.

TLC(n-hexane:ethyl acetate=1:1): Rf 0.46.

(3) Synthesis of (3-aminocyclopentyl)methanol

The azide [prepared in (2)] dissolved in tetrahydrofuran (4 ml) was added dropwise to lithium aluminum hydride (228 mg) dissolved in tetrahydrofuran (4 ml). The mixture was stirred at a room temperature for 30 minutes. The reaction mixture was cooled to 0° C. and then thereto was added a saturated aqueous solution of sodium sulfate. The mixture was stirred for further 30 minutes at a room temperature. The reaction mixture was dried over magnesium sulfate and the evaporated to obtain the title compound having the following physical data.

TLC(methylene chloride:methanol=9:1): Rf 0.05.

Reference Example 2

Synthesis of [3-(4-bromobenzensulfonylamino)cyclopentyl]methanol

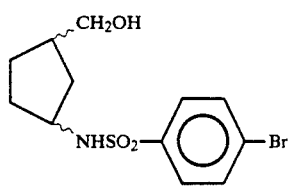

Triethylamine (0.14 ml) was added to the aminoalcohol (prepared in reference example 1, 95 mg) dissolved in benzene (1 ml). The mixture was cooled on an ice-bath. 4-bromobenzenesulfonyl chloride (256 mg) was added to the mixture little by little. The mixture was stirred for 1 hour at a room temperature. Ethyl acetate was added to the reaction mixture. The insoluble material was removed by filtration. The filtrate was concentrated.

The residue was purified by column chromatography on silica gel (n-hexane:ethyl acetate=1:4) to obtain the title compound (144 mg) having the following physical data.

TLC(n-hexane:ethyl acetate=1:3): Rf 0.30.

Reference Example 3

[3-(4-bromobenzenesulfonylamino)cyclopentyl]aldehyde

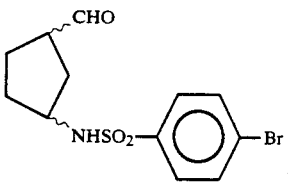

Triethylamine (0.4 ml) was added to the alcohol (prepared in reference example 2, 300 mg) dissolved in dimethyl sulfoxide (1 ml). Sulfur trioxide-pyridine complex (448 mg) dissolved in dimethyl sulfoxide (2 ml) was added dropwise to the mixture at a room temperature. The mixture was stirred for 1 hour. The reaction mixture was poured into ice-water (5 ml). The mixture was extracted with diethyl ether. The extract was washed will water, dried over magnesium sulfate and then evaporated. The residue was purified by column chromatography on silica gel (n-hexane:ethyl acetate=2 obtain the title compound (170 mg) having the following physical data:

TLC(n-hexane:ethyl acetate=1:3): Rf 0.51;

NMR: δ9.67 (0.25H, d), 9.59 (0.75H, d), 7.80–7.60 (4H), 4.89 (0.25H), 4.73 (0.75H), 3.74 (0.25H), 3.61 (0.75H), 2.90 (1H), 2,18 (1H), 2.08–1.36 (6H).

Reference Example 4

[3-(4-methylbenzenesulfonylamino)cyclopentyl]aldehyde

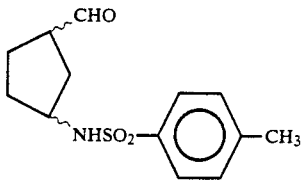

The title compound having the following physical data was obtained, with using aminoalcohol prepared in reference example 1 as a starting materials by the same procedure as reference example 2(4-methylbenzenesulfonyl chloride was sued instead of 4-bromobenzenesulfonyl chloride) and 3.

TLC(n-hexane:ethyl acetate=1:3): Rf 0.49.

Reference Example 5

Methyl (2E)-3-[3-(4-methylbenzenesulfonylamino)cyclopentyl]prop-2-enoate

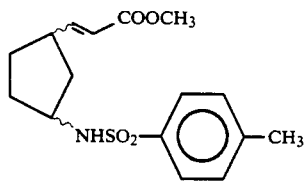

Methoxycarbonyl methyltriphenylphosphorane (705 mg) dissolved in tetrahydrofuran (5 ml) was added to the aldehyde (prepared in reference example 4, 530 mg) dissolved in tetrahydrofuran (5 ml). The mixture was stirred for 10 hours at a room temperature. The reaction mixture was evaporated. The residue was purified by column chromatography on silica gel (n-hexane:ethyl acetate=8:2) to obtain the title compound (560 mg) having the following physical data.

NMR: δ7.70 (2H, d), 7.32 (2H, d), 6.92 (1H, dd), 6.20 (1H, d), 4.42 (1H, d), 3.75 (3H, S), 3.60 (1H, m), 2.43 (3H, S).

Reference Example 6

(2E)-3-[3-(4-methylbenzenesulfonylamino)cyclopentyl]prop-2-enal

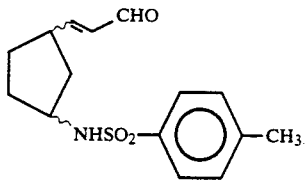

(1) Synthesis of (2E)-3-[3-(4-methylbenzenesulfonylamino)cyclopentyl]prop-2-en-1-ol The methyl carboxylate (prepared in reference example 5, 640 mg) dissolved in toluene (10 ml) was cooled to −78° C. 1.75M solution (2 ml) of diisobutyl aluminum hydrid (DIBAL) in toluene was added dropwise to the cooled mixture. After dropping, the temperature of the solution was raisen to a room temperature. The mixture of methanol and water was added to the reaction mixture to decompose excess DIBAL. The occurred precipitate was removed by filtration. The filtrate was evaporated to obtain the title compound.

(2) Synthesis of (2E)-3-[3-(4-methylbenzenesulfonylamino)cyclopentyl]prop-2-enal Dimethylsulfoxide (312 mg), oxalyl chloride (254 mg) and triethyl amine (600 mg) were added to the alcohol [prepared in (1)] dissolved in methylene chloride (5 ml). The mixture was stirred for 1 hour at −35° C. Water was added to the reaction mixture. The mixture was extracted with ethyl acetate. The extract was washed with water, dried over magnesium sulfate and then evaporated. The residue was purified by column chromatography on silica gel (n-hexane:ethyl acetate=7:3) to obtain the title compound (405 mg) having the following physical data.

NMR: δ9.47 (1H, d), 7.75 (2H, d), 7.31 (2H, d), 6.71 (1H, q), 6.02 (1H, q).

Reference Example 7

3-[3-(4-methylbenzenesulfonylamino)cyclopentyl]propanal

5% palladium carbon (30 mg) was added to the vinylene body (prepared in reference example, 6, 440 mg) in methanol (10 ml). The mixture was stirred for 2 hour in an atmosphere of hydrogen at a room temperature. The catalyst was removed from the reaction mixture. The filtrate was evaporated to obtain the title compound (400 mg) having the following physical data.

NMR: δ9.72 (1H, bs), 7.73 (2H, d), 7.29 (2H, d), 4.42 (1H, d), 3.61 (1H, m), 2.43 (3H, S).

Reference Example 8

Synthesis of (1R*, 2S*, 4R*)-2-(tert-butyldimethyl-silyloxymethyl)bicyclo[2.2.1]heptan-6-one.

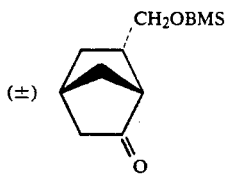

(1) Synthesis of (1R*, 2S*, 4R*, 6R*)-2-hydroxymethylbicyclo[2.2.1]heptan-6-ol (1R*, 2S*, 4R*, 6R*)-bicyclo[2.2.1]heptan-2,6-carbolactone (1.26 g) dissolved in tetrahydrofuran (5 ml) was added dropwise to lithium aluminum hydride (500 mg) suspended in tetrahydrofuran (100 ml) at a room temperature. The mixture was stirred for 1 hour at the same temperature. The mixture was stirred for 1 hour at the same temperature. The mixture of tetrahydrofuran and water was added to the reaction mixture to decompose excess lithium compound. The mixture was filtrated. The filtrate was dried over magnesium sulfate and then evaporated to obtain the title compound.

(2) Synthesis of (1R*, 2S*, 4R*, 6R*)-2-(tert-butyl-dimethylsilyloxy methyl)bicyclo[2.2.1]heptan-6-ol tert-Butyldimethylsilyl chloride (300 mg) was added to the mixture of the diol body [prepared in (1), 260 mg] dissolved in dimethylformamide (2 ml) and imidazole (200 mg). The mixture was stirred at 0° C. for 30 minutes. Ethyl acetate (50 ml) was added to the reaction mixture. The mixture was washed with water, dried over magnesium sulfate and then evaporated to obtain the title compound.

(3) Synthesis of (1R*, 2S*, 4R*)-2-(tert-butyldimethylsilyloxymethyl) bicyclo[2.2.1]heptan-6-one Sarett reagent was prepared form pyridine (5 ml) and anhydrous chromic acid (400 mg). The alcohol [prepared in (2)] dissolved in pyridine (1 ml) was added dropwise to the sarett reagent prepared before. The mixture was left for 30 minutes. Ethyl acetate (30 ml) was added the reaction mixture. The occurred black precipitate was removed by filtration. The filtrate was washed with water, dried over magnesium sulfate and the evaporated. The residue was purified by column chromatography on silica gel (n-hexane:ethyl acetate=9:1) to obtain the title compound (390 mg) having the following physical data.

TLC(n-hexane:ethyl acetate=9:1): Rf 0.60.

Reference Example 9

Synthesis of (1R*, 2S*, 4R*, 6RS*)-2-(tert-butyldimethylsilyloxymethyl)-6-(4-bromobenzenesulfonylamino)-bicyclo[2.2.1]heptane

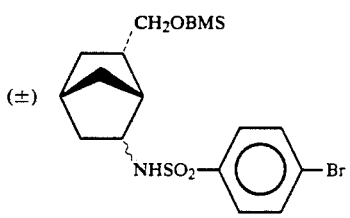

(1) Synthesis of (1R*, 2S*, 4R*, 6RS)-2-(tert-butyl-dimethylsilyloxy methyl)-6-hydroxyiminobicyclo[2.2.1]heptane The ketone (prepared in reference example 8, 240 mg) dissolved in methanol (5 ml) was added to hydroxylamine hydrochloride (210 mg) and barium carbonate (600 mg) suspended in methanol (30 ml). The mixture was refluxed for 2 hours. The reaction mixture was filtered. The filtrate was concentrated. The residue was purified by column chromatography on silica gel (n-hexane:ethyl acetate=7:3) to obtain the title compound.

(2) Synthesis of (1R*, 2S*, 4R*, 6RS*)-2-(tert-butyl-dimethylsilyloxy methyl)-6-aminobicyclo[2.2.1]heptane The oxime compound [prepared in (1)] dissolved in n-propanol (30 ml) was refluxed. In the course of reflux described above, metallic sodium (1 g) was added the refluxing solution little by little. After it was confirmed that sodium was consumed completely, the reaction mixture was cooled to 60° C. Next, n-propanol was removed. Water was added to the reaction solution. The mixture was extracted with eter. The extract was washed with water and evaporated to obtain the title compound (140 mg).

(3) Synthesis of (1R*, 2S*, 4R*, 6RS)-2-(tert-butyl-dimethylsilyloxy methyl)-6-(4-bromobenzenesulfonylamino)bicyclo[2.2.1]heptane 4-Bromobenzenesalfonyl chloride (150 mg) was added to the amine [prepared in (2)] dissolved in pyridine (2 ml). The mixture was stirred at a room temperature for 30 minutes. Ethyl acetate was added tot he reaction mixture. The mixture was washed with water, a saturated aqueous solution of cupric sulfate followed by water, dried over magnesium sulfate and evaporated. The residue was purified by column chromatography on silica gel (n-hexane:ethyl acetate=9:1) to obtain the 6R* isomer body (75 mg) and 6S* isomer (83 mg) having the following physical data.

(a) 6R* isomer

NMR: δ7.72 (2H, d), 7.60 (2H, d), 7.35 (1H, d), 3.80–3.50 (3H, m), 0.96 (9H, S), 0.14 (6H, S).

(b) 6S* isomer

NMR: δ7.75 (2H, d), 7.61 (2H, d), 4.38 (1H, d), 3.60 (1H, m), 3.55 (1H, q), 3.60 (1M, q), 0.85 (9H, S), 0.02 (3H, S), 0.01 (3H, S).

Reference Example 10

[(1R*, 2S*, 4S*, 6R*)-6-(4-Bromobenzenesulfonylamino)cyclopentan-2-yl]methanol

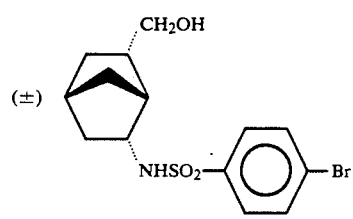

An adequate amount of p-toluenesulfonic acid was added to the silyl ether [prepared in reference example 9 (3)(a), 70 mg] dissolved in methanol (1 ml). The mixture was stirred at a room temperature for 30 minutes. Triethylamine was added to the reaction mixture. The mixture was evaporated. The residue was purified by column chromatography on silica gel (n-hexane:ethyl acetate=7:3) to obtain the title compound (40 mg) having the following physical data.

TLC(n-hexane:ethyl acetate=6:4): Rf 0.50.

Hereinafter, using the silyl ether prepared in reference example 9 (3)(b), the following compound was obtained by the same procedure as described above.

[(1R*, 2S*, 4S*, 6R*)-6-(4-Bromobenzenesulfonylamino)cyclopentan-2-yl]methanol

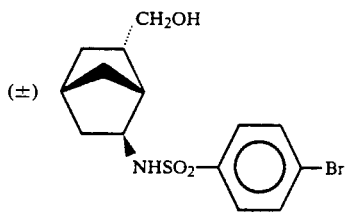

TLC(n-hexane:ethyl acetate=6:4): Rf 0.60.

Reference Example 11

(1R*, 2S*, 4S*, 6R*)-Bicyclo[2.2.1]heptan-N-(4-bromobenzenesulfonyl)-6,2-lactam

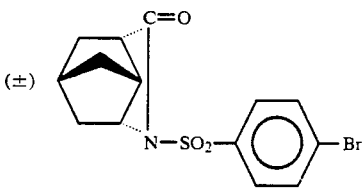

Pyridinium dichromate (376 mg) was added to the alcohol (prepared in reference example 10, 80 mg) dissolved in methylene chloride (10 ml). The mixture was stirred at a room temperature for 3 days. The reaction mixture was filtered. The filtrate was evaporated. The residue was purified by column chromatography on silica gel (ethyl acetate:benzene=1:8) to obtain the title compound (52 mg) having the following physical date.

TLC(ethyl acetate:benzene=1:5): Rf 0.58.

Reference Example 12

(1R*, 2S*, 4S*, 6R*)-Bicyclo[2.2.1]heptan-N-(4-bromobenzenesulfonyl)-6,2-aminoacetal

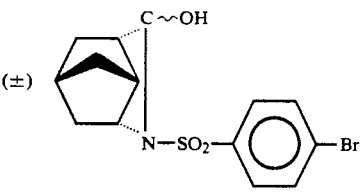

The lactam compound (prepared in reference example 11, 50 mg) dissolved in anhydrous toluene (5 ml) was cooled to −78° C. 1.8M solution of diisobutyl aluminum hydride (DIBAL) in toluene (0.16 ml) was added dropwise to the cooled solution. After the mixture was stirred at −78° C. for 25 minutes, methanol was added to the reaction mixture to decompose excess DIBAL. And then the temperature of the mixture was raised to a room temperature. The reaction mixture was diluted with diethyl ether (50 ml). The mixture was washed with saturated brine, dried over magnesium sulfate and evaporated. The residue was purified by column chromatography on silica gel (ethyl acetate:-benzene=1:8) to obtain the title compound (48 mg) having the following physical data.

TLC (ethyl acetate:benzene=1:5): Rf 0.38.

Reference Example 13

[(1R*, 2S*, 4R*, 6R*)-6-(Tetrahydropyran-2-yloxy)-bicyclo[2.2.1]heptan-2-yl]methanol

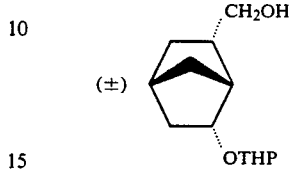

(1) Synthesis of (1R*, 2S*, 4R*, 6R*)-2-(tert-butyldimethylsilyloxy methyl)-6-(tetrahydropyran-2-yloxy)-bicyclo[2.2.1]heptane 2,3-Dihydropyran (200 mg) was added to (1R*, 2S*, 4R*, 6R*)-2-(tert-butyldimethylsilyloxymethyl)bicyclo[2.2.1]heptan-6-ol (prepared in reference example 8(2), 512 mg) dissolved in methylene chloride (3 ml). The mixture was cooled to 0° C. An adequate amount of p-toluenesulfonic acid was added to the mixture. The mixture was stirred at 0° C. for 30 minutes. Triethylamine was added to the reaction mixture. The mixture was washed with water, dried over magnesium sulfate and then evaporated to obtain the title compound.

(2) Synthesis of [(1R*, 2S*, 4S*, 6R*)-6-(Tetrahydropyran-2-yloxy)bicyclo[2.2.1]heptan-2-yl]methanol The equivalent tetrabutylammonium fluoride was added to the BMS ether ]prepared in (1)] dissolve din tetrahydrofran (5 ml). The mixture was stirred at a room temperature for 1 hour. The reaction mixture was diluted with ethyl acetate. The mixture was washed with water followed by saturated brine, dried over magnesium sulfate and then evaporated. The residue was purified by column chromatography on silica gel (n-hexane:ethyl acetate=7:3) to obtain the title compound 400 mg having the following physical data.

TLC(n-hexane:ethyl acetate=7:3): Rf 0.60.

Reference Example 14

(1R*, 2R*, 6R*)-2-Cyanomethyl-6-(tetrahydropyran-2-yloxy)bicyclo [2.2.1]heptane

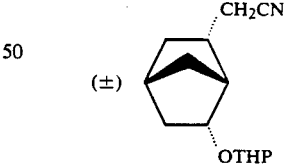

(1) Synthesis of (1R*, 2S*, 4R*, 6R*)-2-mesyloxymethyl-6-(tetrahydropyran-2-yloxy)bicyclo [2.2.1]heptane The title compound was obtained by the same procedure as reference example 1 (1), with using themethanol derivative (prepared in reference example 13).

(2) (1R*, 2R*, 4R*, 6R*)-2-cyanomethyl-6-(tetrahydropyran-2-yloxy) bicyclo[2.2.1]heptane Sodium cyanide (100 mg) was added to the mesylate compound [prepared in (1)] dissolved in hexamethylphosphamide (3 ml). The mixture was stirred at 80° C. for 3 hours. Water was added to the reaction mixture. The mixture was extracted with ethyl acetate. The extract was washed with water and evaporated to obtain the title compound (300 mg) having the following physical data.

IR: ν 2210 cm⁻¹

Reference 15

[1'R*, 2'R*, 4'R*, 6'R*)bicyclo[2.2.1]heptan-2'-yl]aceto-1,6'-lactone

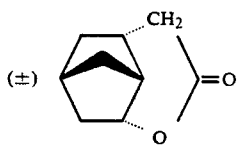

The cyano compound (prepared in reference example 14, 300 mg) was dissolved in the mixture solution of isopropanol (3 ml) and 4N aqueous solution of potassium hydroxide. The mixture solution was refluxed for 16 hours. Concentrated hydrochloric acid (3 ml) was added to the reaction mixture at a room temperature. The mixture was allowed to stand for 2 hours. The mixture was extracted with ethyl acetate. The extract was washed with saturated aqueous solution of sodium bicarbonate followed by saturated brine, dried over magnesium sulfate and then evaporated. The residue was purified by column chromatography on silica gel (n-hexane : ethyl acetate=8 : 2) to obtain the title compound (200 mg) having the following physical data.

IR: ν1780 cm⁻¹

Reference Example 16

(1R, 2S, 3S, 4S)-bicyclo [2.2.1] hept-5-ene-2,3-dicarboxylic acid di(−)-methyl ester

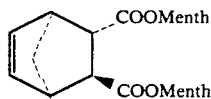

Di-(−)-methyl fumarate (3.82 g) dissolved in toluene (100 ml) was cooled to −78° C. Diethylaluminum chloride (1.49 g) was added dropwise to the mixture. The mixture was stirred for 30 minutes. 1,3-cyclopentadiene (660 mg) distilled freshly was added to the obtained reaction solution. The mixture was stirred for 30 minutes at a temperature of −78° C. and then the temperature of the solution was raised to −20° C. by degrees. 2N hydrochloric acid (200 ml) was added to the reaction mixture. The organic layer was separated. The water layer was extracted twice with ether. The extract was washed with water, dried over sodium sulfate and then evaporated to obtain the title compound (4.2 g) having the following physical data:

NMR(CCl₄ solution): δ 6.20 (2H, S), 4.60 (2H, m), 3.40 (2H, m), 2.55 (2H, m).

Reference Example 17

The mixture of [(1R, 2S, 3S, 4S)-3-carboxybicyclo [2.2.1] hept-5-en-2-yl] carboxylic acid-(−)-methyl ester and the corresponding (1S, 2S, 3S, 4R) compound The mixture of

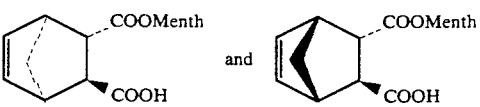

2N aqueous solution of sodium hydroxide (1 ml) was added to dimenthyl ester (1.0 g, prepared in reference example 16) dissolved in ethanol (20 ml). The mixture was refluxed for 30 minutes. The reaction mixture was evaporated. Water (50 ml) was added to the residue. The mixture was extracted with ethyl acetate. The water layer was acidified by adding 1N hydrochloric acid. The mixture was extracted with ethyl acetate. The extract was washed with water, dried over magnesium sulfate and evaporated. The residue was purified by column chromatography on silica gel (ethyl acetate: n-hexane=2:3) to obtain the title compound (320 mg) having the following physical data:

NMR (CCl₄ solution): δ 6.17 (2H), 4.36 (2H), 3.5 ∼2.5 (4H, m).

Reference Example 18

The mixture of [(1R, 2S, 3S, 4S)-3-benzyloxycarbonylamino bicyclo [2.2.1] hept-5-en-2-yl] carboxylic acid menthyl ester and the corresponding (1S, 2S, 3S, 4R) compound The mixture of

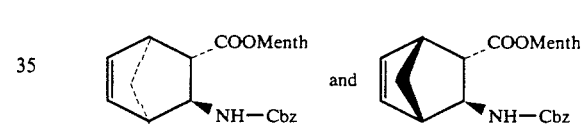

Triethylamine (120 mg) was added to the half ester (320 mg, prepared in reference example 17) dissolved in acetone (5 ml). The solution was cooled to 0° C. Ethyl chloroformate (130 mg) was added dropwise to the solution. The mixture was stirred for 20 minutes. Sodium azide (130 mg) dissolved in water (1 ml) was added to the mixture cooled to 0° C. The mixture was stirred with keeping a same temperature for 30 minutes. The water was added to the reaction mixture. The mixture was extracted three times with toluene to obtain a toluene solution of the corresponding 3-azidecarbonyl body. The solution was dried over magnesium sulfate and then refluxed for 2 hours to obtain the corresponding 3-isocyanate. Benzylalcohol (108 mg) and a catalyst amount of tributylamine were added to the obtained reaction mixture. The reaction mixture was refluxed for 3 hours. The reaction mixture was evaporated. The residue was purified by column chromatography on silica gel (ethyl acetate: n-hexane=1:6) to obtain the title compound (mixture, 340 mg) having the following physical data.

NMR: δ 7.2 (5H), 6.3 (2H), 4.95 (2H, S), 4.35 (2H, m), 2.95 (2H, m).

Reference Example 19

[(1R, 2S, 3S, 4S)-3-benzloxycarbonylamino bicyclo [2.2.1] hept-5-en-2-yl] carboxylic acid menthyl ester or the corresponding (1S, 2S, 3S, 4R) compound

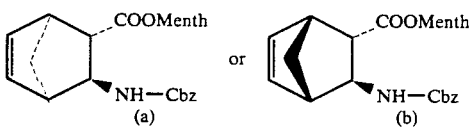

Two isomers obtained in reference example 18 were purified by column chromatography on silica gel (ethyl acetate: n-hexane=3:7) to obtain the title two compounds having the following physical data.

(a) (1R, 2S, 3S, 4S) isomer:
TLC (methylene chloride: n-hexane: ether=12:4:1) : Rf=0.35.

(b) (1S, 2S, 3S, 4R) isomer:
TLC (methylene chloride: n-hexane: ether=12:4:1) : Rf=0.32.

Reference Example 20

[(1R, 2S, 3S, 4S)-3-tosylaminobicyclo [2.2.1]] heptan-2-yl]acetoaldehyde

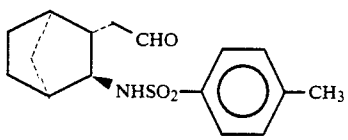

12N hydrochloric acid (0.41 ml) and palladium-carbon (content: 10%, 200 mg) were added to 2-menthyloxycarbonyl-3-benzyloxycarbonylamino compound (prepared in reference example 19(a), 1.08 g) dissolved in anhydrous ethanol (10 ml). The mixture was stirred in an atmosphere of hydrogen, at a room temperature, for 2 hours. The catalyst was removed from the mixture by filtration. The filtrate was evaporated to obtain hydrochloric acid salt of the corresponding amine. The obtained amine was dissolved in pyridine (10 ml). Tosyl chloride (1.24 g) and triethylamine (0.45 ml) were added to the mixture with cooling in an ice-bath. The mixture was stirred at a room temperature for 12 hours. The yellow-orange reaction mixture was poured into 4N hydrochloric acid (50 ml). The mixture was extracted with ethyl acetate (100 ml). The extract was washed with a saturated aqueous solution of sodium bicarbonate, followed by a brine, dried over magnesium sulfate and evaporated. The residue was purified by column chromatography on silica gel (ethyl acetate: n-hexane=1:2) to obtain [(1R, 2S, 3S, 4S)-3-tosylaminobicyclo [2.2.1] heptan-2-yl]carboxylic acid ethyl ester.

Next, in an atmosphere of argon, the ethyl ester obtained before (860 mg) dissolved in anhydrous THF (5 ml) was added dropwise to lithium aluminum hydride (LAH, 186 mg) suspended in anhydrous tetrahydrofuran (THF, 15 ml) at a room temperature. The mixture was stirred for 30 mins. The reaction mixture was cooled to 0° C. The mixture of THF-water (5:2) was added to the mixture to quench excess LAH. The occurred mixture such as rice gruel was dissolved by adding 1N hydrochloric acid (30 ml). The mixture was extracted three times with ethyl acetate (20 ml). The extract was dried over magnesium sulfate and then evaporated to obtain the corresponding alcohol (white solid, 683 mg).

Next, alcohol described above (309 mg) was dissolved in dimethyl sulfoxide (DMSO, 5 ml). Triethylamine (0.5 ml) was added to the solution. Trioxide-pyridine complex (477 mg) dissolved in DMSO (2 ml) was added dropwise to the solution. The mixture was stirred at a room temperature for 1 hours, poured into ice-water (30 ml) and extracted twice with ethyl acetate (20 ml). The extract was dried over magnesium sulfate and then evaporated.

The obtained residue was purified by column chromatography on silica gel (ethyl acetate: methylene chloride=1.10) to obtain [(1R, 2S, 3S, 4S)-3-tosyl aminobicyclo [2.2.1] heptan-2-yl] aldehyde (287 mg, white solid).

Next, 1.4M solution (2.1 ml) of n-butyllithium in hexane was added dropwise to diisopropylamine (0.5 ml) dissolved in tetrahydrofuran (THF, 3 ml) at a temperature of 0° C. The mixture was stirred for 15 minutes to obtained a solution of lithiumdiisopropylamide (LDA).

Next, a solution of LDA prepared before was added dropwise to 4-chlorophenoxymethyl-triphenylphosphoniumchloride (1.32 g) suspended in THF (10 ml) at a temperature of 0° C. to obtain a deep red solution.

Aldehyde (287 mg) prepared before dissolved in THF (5 ml) was added dropwise to the solution. The solution was stirred at a temperature of 0° C. minutes. The reaction mixture was poured into ice-water (30 ml). The mixture was extracted twice with ethyl acetate (50 ml). The extract was dried over magnesium sulfate and evaporated. The residue was purified by column chromatography on silica gel (ethyl acetate: n-hexane=1:3) to remove polar substances. Enol ether obtained before was concentrated 1.4- dioxane (10 ml) and 4N hydrochloric acid (2 ml) were added to the residue. The mixture was stirred at 80° C. for 40 minutes. Ice cooled 10% aqueous solution of sodium hydroxide (30 ml) was added to the mixture. The mixture was extracted twice with ethyl acetate (50 ml). The extract was dried over magnesium sulfate and evaporated to obtain the title compound having the following physical data. The compound was used in next step without purification.

NMR: δ 9.75 (1H, bs), 7.75 (2H, d), 7.30 (2H, d);
MS: m/e 307 ($M^{30}$), 289, 278.

Reference Example 21

(5Z)-7-[(1R, 2S, 3S, 4S)-3-tosylaminobicyclo [2.2.1] heptan-2-yl]hept-5enoic acid

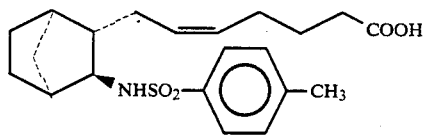

Potassium tert-butoxide (740 mg) was added to 4-carboxybutyltriphenylphosphoniumbromide (1.33 g) suspended in toluene (10 ml). The mixture was stirred at a temperature of 80° C. for 40 minutes. The obtained reaction solution was cooled to 0° C. [(1R, 2S, 3S, 4S)-3-tosylaminobicyclo [2.2.1] heptan-2-yl]acetaldehyde (270 mg; prepared in reference example 20) dissolved in toluene (3 ml) was added dropwise to the solution. The solution was stirred at a temperature of 0° C. for 15 minutes. The reaction mixture was poured into ice-water. The mixture was extracted three times with ether (20 ml) to remove neutral substances and basic substances. The water layer was acidified with 1N hydrochloric acid (10 ml). The solution was extracted twice with ethyl acetate (30 ml). The extract was dried over magnesium sulfate and evaporated. The residue was purified by column chromatography on silica gel (methylene chloride: methanol=100:1→25:1) to obtain the title compound (222 mg) having the following physical data:

TLC (methylene chloride: methanol=10:1): Rf 0.45;
NMR: δ 7.75 (2H, d), 7.28 (2H, d), 5.26 (2H, m), 5.11 (1H, d), 3.00 (1H, broad), 2.42 (3H, S), 2.37 (2H, t), 2.16~0.87 (15H);
MS: m/e 391 (M+), 373;
m.p.: 77°~78° C.; feature: white crystal.

EXAMPLE 1

(5Z)-6-[3-(4-bromobenzenesulfonylamino)cyclopentyl]hex-5-enoic acid

Tetrahydrofuran (1 ml) was added to the mixture of 4-carboxbutyltriphenylphosphonium bromide (602 mg) and potassium tertbutoxide (306 mg) in an atmosphere of argon. The mixture was stirred at a room temperature for 15 minutes to obtain the ylide compound. The aldehyde (prepared in reference example 3, 150 mg) dissolved in tetrahydrofuran (0.5 ml) was added dropwise to the mixture. The mixture was stirred at a room temperature for 30 minutes. The reaction mixture was poured into ice water (10 ml). The mixture was extracted with diethyl ether. The extract was dried over magnesium sulfate and then filtered. Then, the solution was evaporated. The residue was purified by column chromatography on silica gel (methylene chloride: methanol=97 : 3) to obtain the title compound (130 mg) having the following physical data.

TLC (methylene chloride : methanol=9 : 1) : Rf 0.48;
NMR : δ 7.79~7.58 (4H), 5.36~5.18 (2H0, 5.10 (2/3H, d), 4.75 (1/3H, d), 3.80~3.53 (1H), 3.00~2.50 (1H), 2.43~2.22 (2H), 2.18~1.00 (10H);
IR : ν 3240, 2920, 1700, 1560, 1420, 1110, 1045 cm $^{-1}$;
MS : m/z 417, 415, 400, 398, 355, 300.

EXAMPLE 1(A)~1(CÇ)

Hereinafter, the compounds 1(a)~1(o) shown in the following table III were obtained by the same procedure as reference example 1, 2, 3 and example 1, with using the corresponding 3-hydroxycyclo (or bicyclo) alkyl carboxylic acid ester as starting material, with the proviso that 4-methylbenzenesulfonyl chloride was used instead of 4-bromobenzenesulfonyl chloride in example 1(n) and 1(o).

And the compounds 1(p)~1(bb) shown in the following table III were obtained by the same procedure as reference examples 2, 3 and example 1, with using the corresponding aminoalcohol, with the proviso that benzenesulfonyl chloride was used in example 1(q), 4-methylbenzenesulfonyl chloride was used in example 1(s), 1(w), 10(x), 1(z) and 1(aa), instead of 4-bromobenzenesulfonyl chloride.

TABLE III

| Example No. | Structural formula | Name | TLC | other physical data |
|---|---|---|---|---|
| 1 (a) | (±), COOH, Br, NHSO$_2$ | (5Z)-6-[(1R*, 2R*, 4S*, 6S*)-6-(4-bromobenzenesulfonylamino)bicyclo[2.2.2]octan-2-yl]hex-5-enoic acid | Rf 0.15 (n-hexane:ethyl acetate = 1:3) | IR(KBr method): 3400, 3270, 2940, 1710, 1580, 1440, 1320, 1160, 1095, 1070, 740, 610 cm$^{-1}$ |
| 1 (b) | (±), COOH, Br, NHSO$_2$ | (5Z)-6-[(1R*, 2S*, 4R*, 6S*)-6-(4-bromobenzenesulfonylamino)bicyclo[2.2.1]heptan-2-yl]hex-5-enoic acid | — | MS: m/e 441, 443(M$^+$), 368, 370, 222 |
| 1 (c) | (±), COOH, Br, NHSO$_2$ | (5Z)-6-[(1R*, 2R*, 4R*, 6S*)-6-(4-bromobenzenesulfonylamino)bicyclo[2.2.1]heptan-2-yl]hex-5-enoic acid | — | MS: m/e 441, 443(M$^+$), 368, 370, 336, 328, 222, 206 |
| 1 (d) | (±), COOH, Br, NHSO$_2$ | (5Z)-6-[(1R*, 2R*, 4R*, 6R*)-6-(4-bromobenzenesulfonylamino)bicyclo[2.2.1]heptan-2-yl]hex-5-enoic acid | Rf 0.15 (ethyl acetate:n-hexane = 3:1) | MS: m/e 441(M$^+$), 423, 368, 340 |
| 1 (e) | (±), COOH, Br, NHSO$_2$ | (5Z)-6-[(1R*, 2R*, 4S*, 6R*)-6-(4-bromobenzenesulfonylamino)bicyclo[2.2.2]octan-2-yl]hex-5-enoic acid | Rf 0.15 (ethyl acetate:n-hexane = 3:1) | MS: m/e 455(M$^+$) |

TABLE III-continued

| Example No. | Structural formula | Name | TLC | other physical data |
|---|---|---|---|---|
| 1 (f) | (±) (less polar isomer) | (5Z)-6-[(1R*, 2S*, 4S*, 6RS)-6-(4-bromobenzenesulfonylamino)bicyclo[2.2.2]octan-2-yl]hex-5-enoic acid | Rf 0.32 (ethyl acetate:n-hexane = 2:1) | MS: m/e 455(M$^+$), 439, 395, 342, 312, 300, 287 |
| 1 (g) | (±) (more polar isomer) | (5Z)-6-[(1R*, 2R*, 4S*, 6RS)-6-(4-bromobenzenesulfonylamino)bicyclo[2.2.2]octan-2-yl]hex-5-enoic acid | Rf 0.24 (ethyl acetate:n-hexane = 2:1) | MS: m/e 455(M$^+$), 437, 419, 409, 395, 342, 302, 287 |
| 1 (h) | | (5Z)-6-[(1R, 3R)-3-(4-bromobenzenesulfonylamino)cyclopentyl]hex-5-enoic acid | Rf 0.24 (ethyl acetate:n-hexane = 3:1) | MS: m/e 415, 397, 369, 355, 300, 274, 196, 162 |
| 1 (i) | | (5Z)-6-[(1R, 3S)-3-(4-bromobenzenesulfonylamino)cyclopentyl]hex-5-enoic acid | Rf 0.30 (ethyl acetate n-hexane = 3:1) | MS: m/e 415(M$^+$), 397, 369, 355, 300, 274 |

TABLE III-continued

| Example No. | Structural formula | Name | TLC | other physical data |
|---|---|---|---|---|
| 1 (j) | COOH, Br, NHSO$_2$ (cyclopentyl) | (5Z)-6-[(1S, 3S)-3-(4-bromobenzenesulfonylamino)cyclopentyl]hex-5-enoic acid | Rf 0.24 (ethyl acetate n-hexane = 3:1) | MS: m/e 415, 397, 355, 300, 274, 219, 196 |
| 1 (k) | COOH, Br, NHSO$_2$ (cyclopentyl) | (5Z)-6-[(1S, 3R)-3-(4-bromobenzenesulfonylamino)cyclopentyl]hex-5-enoic acid | Rf 0.30 (ethyl acetate n-hexane = 3:1) | MS: m/e 415, 397, 369, 355, 300, 274, 196, 162 |
| 1 (l) | COOH, Br, NHSO$_2$ (cyclohexyl) (±) | (5Z)-6-[(1S*, 3S*)-3-(4-bromobenzenesulfonylamino)cyclohexyl]hex-5-enoic acid | Rf 0.27 (ethyl acetate:n-hexane = 3:1) | MS: m/e 429(M$^+$), 411, 314, 274 |
| 1 (m) | COOH, Br, NHSO$_2$ (cyclohexyl) (±) | (5Z)-6-[(1R*, 3S*)-3-(4-bromobenzenesulfonylamino)cyclohexyl]hex-5-enoic acid | Rf 0.30 (ethyl acetate:n-hexane = 3:1) | MS: m/e 429(M$^+$), 411, 383, 314, 274 |
| 1 (n) | COOH, CH$_3$, NHSO$_2$ (cyclopentyl) | (5Z)-6-[(1R, 3S)-3-tosylaminocyclopentyl]hex-5-enoic acid | Rf 0.25 (ethyl acetate:n-hexane = 3:1) | MS: m/e 351(M$^+$), 333, 305, 291, 236, 210, 196, 180, 162, 155 |

TABLE III-continued

| Example No. | Structural formula | Name | TLC | other physical data |
|---|---|---|---|---|
| 1 (o) | (structure) | (5Z)-6-[(1R, 3R)-3-tosylaminocyclopentyl]hex-5-enoic acid | Rf 0.25 (ethyl acetate:n-hexane = 3:1) | MS: m/e 351(M+), 333, 291, 236, 210, 196, 180 |
| 1 (p) | (structure) | (5Z)-6-[(1R*, 2R*, 3S*, 4S*)-3-[N-tosylaminomethyl]bicyclo[2.2.1]heptan-2-yl]hex-5-enoic acid | Rf 0.45 (methylene chloride:methanol = 10:1) | MS: m/e 391(M+), 373, 331, 305, 290 |
| 1 (q) | (structure) | (5Z)-6-[(1R, 2R, 3S, 4S)-3-(N-benzenesulfonylaminomethyl)bicyclo[2.2.1]heptan-2-yl]hex-5-enoic acid | — | MS: m/e 359(M-18), 317, 276, 220, 133 |
| 1 (r) | (structure) | (5Z)-6-[(1R, 2R, 3S, 4S)-3-[N-(4-bromobenzenesulfonyl)aminomethyl]bicyclo[2.2.1]heptan-2-yl]hex-5-enoic acid | Rf 0.30 (ethyl acetate) | MS: m/e 455, 457, 437, 439, 395, 397, 342, 344, 218 |
| 1 (s) | (structure) | (5Z)-6-[(1S, *2S*, 3S*, 4R*)-3-[N-tosylaminomethyl]bicyclo[2.2.1]heptan-2-yl]hex-5-enoic acid | Rf 0.45 (n-hexane:ethyl acetate = 1:1) | MS: m/e 391(M+), 373, 332, 290 |
| 1 (t) | (structure) | (5Z)-6-[(1R*, 2S*)-2-[N-(4-bromobenzenesulfonyl)aminomethyl]cyclohexan-1-yl]hex-5-enoic acid | Rf 0.45 (n-hexane:ethyl acetate = 1:1) | MS: m/e 443(M+), 425, 383, 342, 330 |

TABLE III-continued

| Example No. | Structural formula | Name | TLC | other physical data |
|---|---|---|---|---|
| 1 (u) | | (5Z)-6-[(1R, 2R, 3S, 4S)-3-[2-[N-(4-bromobenzenesulfonyl)amino]ethyl]bicyclo[2.2.1]heptan-2-yl]hex-5-enoic acid | Rf 0.33 (n-hexane:ethyl acetate = 1:1) | MS: m/e 469(M+), 451, 423, 409 |
| 1 (v) | | (5Z)-6-[(1R, 2S*)-2-[N-(4-bromobenzenesulfonyl)aminomethyl]cyclopentan-1-yl]hex-5-enoic acid | Rf 0.13 (n-hexane:ethyl acetate = 1:1) | MS: m/e 429(M+), 411, 369, 328, 314, 248 |
| 1 (w) | | (5Z)-6-[(1R, 2S*)-2-[N-tosylaminomethyl]cyclopentan-1-yl]hex-5-enoic acid | Rf 0.13 (n-hexane:ethyl acetate = 1:1) | MS: m/e 365(M+), 347, 305, 264, 250, 210 |
| 1 (x) | | (5Z)-6-[(1S, 2S, 3R, 4R)-3-[N-tosylaminomethyl]bicyclo[2.2.1]heptan-2-yl]hex-5-enoic acid | Rf 0.22 (n-hexane:ethyl acetate = 1:1) | MS: m/e 391(M+), 378, 331, 236, 220 |
| 1 (y) | | (5Z)-6-[(1S, 2S, 3R, 4R)-3-[N-(4-bromobenzenesulfonyl)aminomethyl]bicyclo[2.2.1]heptan-2-yl]hex-5-enoic acid | Rf 0.36 (n-hexane:ethyl acetate = 1:1) | MS: m/e 455, 437, 395, 342, 248, 236 |
| 1 (z) | | (5Z)-6-[(1R, 2R, 3S, 4S)-3-[N-aminomethyl]bicyclo[2.2.1]heptan-2-yl]hex-5-enoic acid | Rf 0.22 (n-hexane:ethyl acetate = 1:1) | MS: m/e 391(M+), 373, 332, 236, 220 |

TABLE III-continued

| Example No. | Structural formula | Name | TLC | other physical data |
|---|---|---|---|---|
| 1 (aa) | (structure with COOH, CH₃, NHSO₂) | (5Z)-6-[(1R, 4S, 5R, 6R)-6-[N-(4-methylbenzenesulfonyl)aminomethyl]bicyclo[2.2.1]hept-2-en-5-yl]hex-5-enoic acid | Rf 0.35 (n-hexane:ethyl acetate = 1:1) | MS: m/e 389(M+), 272, 218 |
| 1 (bb) | (structure with COOH, Br, NHSO₂) | (5Z)-6-[(1R, 4S, 5R, 6R)-6-[N-(4-bromobenzenesulfonyl)aminomethyl]bicyclo[2.2.1]hept-2-en-5-yl]hex-5-enoic acid | Rf 0.51 (ethyl acetate n-hexane = 1:1) | MS: m/e 453(M+), 219 |
| 1 (cc) | (structure with COOH, Br, NHSO₂) | (5E)-6-[(1S, 2S, 3R, 4R)-3-[N-(4-bromobenzenesulfonyl)aminomethyl]bicyclo[2.2.1]heptan-2-yl]hex-5-enoic acid | Rf 0.25 (ethyl acetate n-hexane = 1:1) | MS: m/e 455(M+), 435, 395, 354, 342 |

EXAMPLE 2

(5Z, 7E)-8-[3-(4-methylbenzenesulfonylamino)cyclopentyl]oct-5,7-dienoic acid

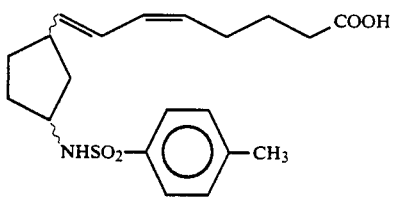

The title compound having the following physical data was obtained by the same procedure as example 1, with using the aldehyde prepared in reference example 6 as a starting material.

TLC (methylene chloride : methanol = 9 : 1) : Rf 0.44;
NMR : δ 6.27 (1H, dd), 5.98 (1H), 5.85 (1H, dd), 5.50 (1H), 5.32 (1H), 3.63 (1H), 2.62~1.06 (16H), 0.98~0.76 (1H);
MS : m/z 377, 359, 331, 317, 264, 250, 236, 222, 155, 91.

EXAMPLE 2(A)

The following compound was obtained by the same procedure as example 2, with using the aldehyde prepared in reference example 7. (5Z)-8-[3-(4-methylbenzenesulfonylamino)cyclopentyl]oct-5-enoic acid

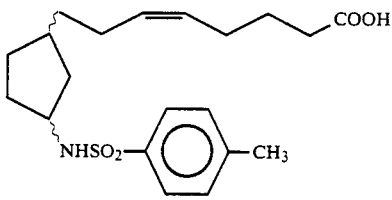

TLC (methylene chloride :P methanol = 9 : 1) : Rf 0.50;
NMR : δ 7.74 (2H, d), 7.28 (2H, d), 5.50~5.18 (2H, m), 4.98~4.78 (1H, m), 3.79~3.66 (1H, m), 2.42 (3H, S), 2.30 (2H, t), 2.19~1.16 (14H, m), 1.16~0.80 (1H, m);
IR : ν 3250, 2930, 1700, 1440, 1320, 1150, 1090, 900, 810, 655 cm$^{-1}$;
MS : m/z 379 (M+), 361, 333, 319, 278, 266, 250, 236, 224, 206, 190, 172, 155, 91.

EXAMPLE 3

Methyl (5Z)-6[(1R*, 2R*, 4R*, 6R*)-6-(4-bromobenzenesulfonylamino) bicyclo[2.2.1]heptan-2-yl hex-5-enoate

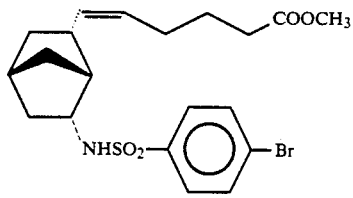

4-carboxybutyltriphenylphosphonium bromide (487 mg) and potassium tert-butoxide (247 mg) were added to anhydrous tetrahydrofuran (10 ml). The mixture was stirred at a room temperature for 20 minutes to obtain the ylide compound. The obtained solution was cooled to 0° C. the lactim compound (prepared in reference example 12, 82 mg) dissolved in anhydrous tetrahydrofuran (5 ml) was added dropwise to the cooled solution. The mixture was stirred at 0° C. for 15 minutes. Cooled 1N hydrochloric acid (20 ml) was added to the reaction mixture. The mixture was extracted with ethyl acetate. The extract was dried over magnesium sulfate and then evaporated to obtain the carboxylic acid corresponding to the desired compound. The obtained residue was dissolved in methylene chloride (5 ml). A solution of diazomethane in ether was added to the solution at 0° C. till the reaction mixture showed yellow. The reaction solution was evaporated. The residue was purified by colum chromatography on silica gel (n-hexane : ethyl acetate = 3 : 1) to obtain the title compound (46 mg) having the following physical data.

TLC (n-hexane : ethyl acetate = 5 : 1) : Rf 0.30:
NMR : δ 7.68 (4H, m), 5.65~5.30 (2H, m), 5.23 (1H, d), 3.68 (3H, S), 3.64 (1H, m).

EXAMPLE 3 (A)

The following compound was obtained by the same procedure as example 3, with using the carboxylic acid prepared in example 1(i). Methyl (5Z)-6-[(1R,3S)-3-(4-bromobenzenesulfonylamino)cyclopentyl]hex-5-enoate

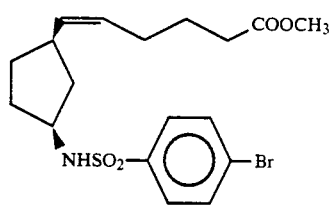

TLC (ethyl acetate : benzene = 1 : 8) :Rf 0.30;
MS : m/z 429 (M+), 397, 369, 355, 346, 325, 316, 300.

EXAMPLE 4 AND 4 (A)

(5Z)-7-[(1R*, 2R*, 4R*, 6S*)-6-(4-methylbenzenesulfonylamino)bicyclo [2.2.1]heptan-2-yl]hept-5-enoic acid and the corresponding (1R*, 2R*, 4R*, 6R*) isomer

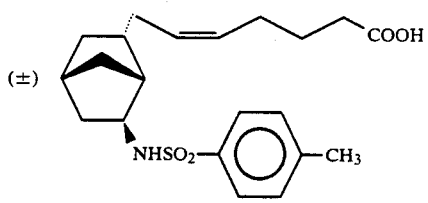

and

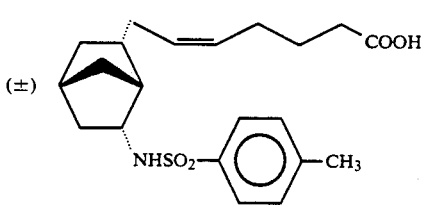

The title compound having the following physical data (both 6S* isomer and 6R* isomer), was obtained by the procedure as reference example 8, 9, 10 and example 1, with using the carbolactone compound prepared in reference example 15 as a starting material.

Example 4 (1R*, 2R*, 4R*, 6S*) isomer

TLC (ethyl acetate) : Rf 0.80;

NMR : δ 7.75 (2H, d), 7.29 (2H, d), 5.27 (2H, m), 4.55 (1H, d), 3.49 (1H, m), 2.43 (3H, S), 2.36 (2H, t), )0.50 (1H, broad d);

MS : m/z 391 (M+), 373, 349, 345, 318, 236, 218, 155, 91. Example 4(a) (1R*, 2R*, 4R*, 6R*) isomer TLC (ethylacetate) : Rf 0.60;

NMR : δ 7.77 (2H, d), 7.29 (2H, d), 5.63 (1H, d), 5.38 (2H, m), 3.52 (1H, m), 1.42 (3H, S), 1.28 (2H, broad S), 0,80 (2H, m);

MS : m/z 391 (M+), 373, 342, 318, 304, 293, 236.

EXAMPLE 5

Octyl (5Z)-6-[3-(4-bromobenzenesulfonylamino)cyclopentyl]hex-5-enoate

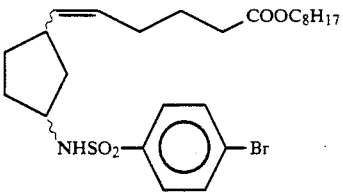

The carboxylic acid (prepared in reference example 1, 100 mg) was dissolved in oxalyl chloride (0.5 ml). The solution was stirred at a room temperature for 1 hour. The reaction solution was evaporated to remove excess oxalyl chloride. The residue was dissolved in pyridine (3 ml). n-Octylalcohol (100 mg) was added to the solution. The mixture was stirred at a room temperature for 2 hours. Ethyl acetate was added to the reaction mixture. The mixture was washed with water, dried over magnesium sulfate and then evaporated. The residue was purified by column chromatography on silica gel (n-hexane : ethyl acetate=9 : 1) to obtain the title compound (110 mg) having the following physical data.

TLC (n-hexane : ethylacetate=9 : 1) : Rf 0.5;

NMR : δ 7.7 (4H, m), 5.25 (2H, m) 4.70 and 4.62 (1H, each d), 4.66 and 4.20 (2H, each t), 3.71 and 3.60 (1H, each m), 0.92 (3H, broad t).

EXAMPLE 5(A)~5(Q)

The ester compounds showed in the following Table IV were obtained by the same procedure as example 5, with using the corresponding acid and the suitable alcohols.

TABLE IV

| Example No. | Structural formula | Name | TLC | MS(m/e) |
|---|---|---|---|---|
| 5 (a) | [structure: cyclopentane with COOC₂H₅ chain and 4-bromophenyl-NHSO₂ group] | ethyl(5Z)-6-[(1R, 3S)-3-(4-bromobenzenesulfonylamino)cyclopentyl]hex-5-enoate | Rf 0.22 (n-hexane: ethyl acetate = 3:1) | 443(M⁺), 397, 356, 314, 300 |
| 5 (b) | [structure: cyclopentane with COOCH(CH₃)₂ chain and 4-bromophenyl-NHSO₂ group] | isopropyl(5Z)-6-[(1R, 3S)-3-(4-bromobenzenesulfonylamino)cyclopentyl]hex-5-enoate | Rf 0.25 (n-hexane: ethyl acetate = 3:1) | 457(M⁺), 415, 397, 369, 355, 314, 300 |
| 5 (c) | [structure: cyclopentane with menthyl ester chain and 4-bromophenyl-NHSO₂ group] | l-menthyl(5Z)-6-[(1R, 3S)-3-(4-bromobenzenesulfonylamino)cyclopentyl]hex-5-enoate | Rf 0.43 (benzene: ethyl acetate = 8:1) | 553(M⁺), 538, 521, 415, 397, 369, 355, 314, 300 |
| 5 (d) | [structure: bicyclo[2.2.1]heptane with COOC₂H₅ chain and 4-bromophenyl-NHSO₂ group via aminomethyl] | ethyl(5Z)-6-[(1S, 2S, 3R, 4R)-3-[N-(4-bromobenzenesulfonyl)aminomethyl]bicyclo[2.2.1]heptan-2-yl]]hex-5-enoate | Rf 0.40 (n-hexane: ethyl acetate = 2:1) | 485, 483, 437, 395, 342, 264, 248 |

TABLE IV-continued

| Example No. | Structural formula | Name | TLC | MS(m/e) |
|---|---|---|---|---|
| 5 (e) | 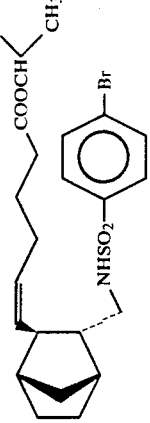 | isopropyl(5Z)-6-[(1S, 2S, 3R, 4R)-3-[N-(4-bromobenzenesulfonyl)aminomethyl]bicyclo[2.2.1]heptan-2-yl]hex-5-enoate | Rf 0.46 (n-hexane: ethyl acetate = 2:1) | 499(M+), 497(M+), 437, 409, 395, 342, 278, 262, 220 |
| 5 (f) | 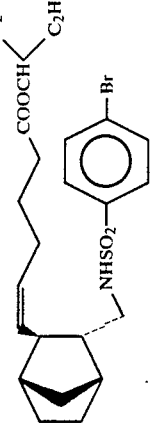 | 1-ethylpropyl(5Z)-6-[(1S, 2S, 3R, 4R)-3-[N-(4-bromobenzenesulfonyl)aminomethyl]bicyclo[2.2.1]heptan-2-yl]hex-5-enoate | Rf 0.42 (n-hexane: ethyl acetate = 2:1) | 527(M+, 81Br), 525 (M+, 79Br), 455, 437, 395, 342, 306, 290, 248, 236, 220, 203 |
| 5 (g) | 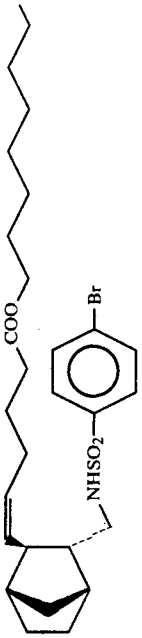 | octyl(5Z)-6-[(1S, 2S, 3R, 4R)-3-[N-(4-bromobenzenesulfonyl)aminomethyl]bicyclo[2.2.1]heptan-2-yl]hex-5-enoate | Rf 0.50 (n-hexane: ethyl acetate = 9:1) | 569, 567, 437, 395, 348, 332, 320 |
| 5 (h) |  | menthyl(5Z)-6-[(1S, 2S, 3R, 4R)-3-[N-(4-bromobenzenesulfonyl)aminomethyl]bicyclo[2.2.1]heptan-2-yl]hex-5-enoate | Rf 0.51 (n-hexane: ethyl acetate = 2:1) | 595(M+, 81Br), 593 (M+, 79Br), 455, 437, 395, 220 |
| 5 (i) | 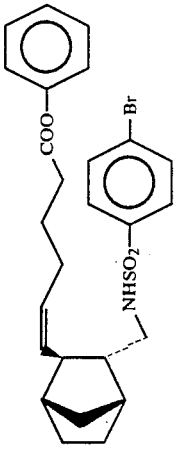 | phenyl(5Z)-6-[(1S, 2S, 3R, 4R)-3-[N-(4-bromobenzenesulfonyl)aminomethyl]bicyclo[2.2.1]heptan-2-yl]hex-5-enoate | Rf 0.35 (benzene: ethyl acetate = 3:1) | 531(M+), 472, 438, 395, 354, 342 |

TABLE IV-continued

| Example No. | Structural formula | Name | TLC | MS(m/e) |
|---|---|---|---|---|
| 5 (j) | | (5Z)-6-[(1S, 2S, 3R, rR)-3-[N-(4-bromobenzenesulfonyl)amino methyl]bicyclo[2.2.1]heptan-2-yl]hex-5-enoic acid cholesterol ester | Rf 0.42 (n-hexane: ethyl acetate = 3:1) | 823(M+), 531, 455, 438, 393 |
| 5 (k) | | t-butyl(5Z)-6-[(1S, 2S, 3R, 4R)-3-[N-(4-bromobenzenesulfonyl)aminomethyl]bicyclo[2.2.1]heptan-2-yl]hex-5-enoic acid | Rf 0.35 (n-hexane: ethyl acetate = 3:1) | 454(M-t-/butyl), 437, 409, 395, 352, 340 |
| 5 (l) | | n-hexyl(5Z)-6-[(1S, 2S, 3R, 4R)-3-[N-(4-bromobenzenesulfonyl)aminomethyl]bicyclo[2.2.1]heptan-2-yl]hex-5-enoic acid | Rf 0.37 (n-hexane: ethyl acetate = 3:1) | 539(M+), 437, 395, 354, 342 |
| 5 (m) | | n-decyl(5Z)-6-[(1S, 2S, 3R, 4R)-3-[N-(4-bromobenzenesulfonyl)aminomethyl]bicyclo[2.2.1]heptan-2-yl]hex-5-enoate | Rf 0.40 (n-hexane: ethyl acetate = 3:1) | 595(M+), 456, 437, 404, 388, 376, 360 |
| 5 (n) | | dodecyl(5Z)-6-[(1S, 2S, 3R, 4R)-3-[N-(4-bromobenzenesulfonyl)aminomethyl]bicyclo[2.2.1]heptan-2-yl]hex-5-enoate | Rf 0.42 (n-hexane: ethyl acetate = 3:1) | 624(M+), 456, 437, 404, 395, 389, 376, 360 |

TABLE IV-continued

| Example No. | Structural formula | Name | TLC | MS(m/e) |
|---|---|---|---|---|
| 5 (o) | | (5Z)-6-[(1S, 2S, 3R, 4R)-3-[N-(4-bromobenzenesulfonyl)amino methyl]bicyclo[2.2.1]heptan-2-yl]hex-5-enoic acid borneol ester | Rf 0.50 (n-hexane: ethyl acetate = 8:1) | 591(M+), 455, 437, 395, 220 |
| 5 (p) | | cyclohexyl(5Z)-6-[(1S, 2S, 3R, 4R)-3-[N-(4-bromobenzene sulfornyl)aminomethyl]bicyclo [2.2.1]heptan-2-yl]hex-5-enoate | Rf 0.56 (n-hexane: ethyl acetate = 1:1) | 537(M+), 455, 437, 409, 395, 354, 432 |
| 5 (q) | | n-butyl(5Z)-6-[(1S, 2S, 3R, 4R)-3-[N-(4-bromobenzenesulfonyl) aminomethyl]bicyclo[2.2.1] heptan-2-yl]hex-5-enoate | Rf 0.40 (n-hexane: ethyl acetate = 2:1) | 511(M+), 436, 394, 353, 341, 292 |

EXAMPLE 6

(5Z)-7-[(1R, 2S, 3S, 4S)-3-tosylaminobicyclo [2.2.1] heptane-2-yl]hept-5-enamide amines instead of ammonia gas in example 6(a) and 6(b), and using the corresponding acid instead of an acid prepared in reference example 21 in example 6(c) and 6(d).

TABLE V

| Example No. | Structural formula | Name | TLC | MS(m/e) |
|---|---|---|---|---|
| 6 (a) | | (5Z)-N-methyl-7-[(1R, 2S, 3S, 4S)-3-tosylaminobicyclo[2.2.1]heptan-2-yl]hept-5-enamide | Rf 0.35 (ethyl acetate: n-hexane = 5:1) | 404($M^+$), 332, 318, 290, 278, 264, 250 |
| 6 (b) | | (5Z)-N,N-dimethyl-7-[(1R, 2S, 3S, 4S)-3-tosylaminobicyclo[2.2.1]heptan-2-yl]hept-5-enamide | Rf 0.35 (ethyl acetate: n-hexane = 5:1) | 418($M^+$), 374, 332, 318, 290, 264, 218 |
| 6 (c) | | (5Z)-6-[(1R, 3S)-3-(4-bromobenzenesulfonylamino)cyclopentyl]hex-5-enamide | Rf 0.13 (ethyl acetate: n-hexane = 3:1) | 414($M^+$), 356, 300, 236, 219 |
| 6 (d) | | (5Z)-6-[(1S, 2S, 3R, 4R)-3[N-(4-bromobenzenesulfonyl)aminomethyl]bicyclo[2.2.1]heptan-2-yl]hex-5-enamide | Rf 0.22 (ethyl acetate: n-hexane = 2:1) | 456($M^+$, $^{81}Br$), 454 ($M^+$, $^{79}Br$), 437, 398, 354, 342, 248, 235, 219 |

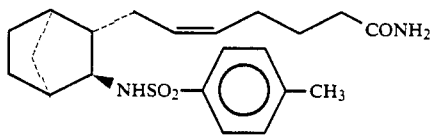

Oxalyl chloride (2 ml) was added to (5Z)-7-[(1R, 2S, 3S, 4S)-3-tosylaminobicyclo [2.2.1] heptan-2-yl]hep-5-tenoic acid (100 mg, prepared in reference example 21). The mixture was stirred at a room temperature for 1 hour. Excess oxalyl chloride was removed from the mixture in vacuo to obtain an acid chloride. This acid chloride was dissolved in methylene chloride (5 ml). The solution was cooled to 0° C. and became turbid by blowing ammonia gas through the solution. The mixture was stirred at a room temperature for 30 mins. The insoluble substance was removed by filtration. The filtrate was concentrated. The residue was purified by column chromatography on silica gel (ethyl acetate: hexane=1:1→5:1) to obtain the title compound 81.4 mg having the following physical data:

TLC (ethyl acetate: hexane=5:1): Rf 0.35;

NMR: δ 7.76 (2H, d), 7.27 (2H, d), 5.80 (1H, broad), 5.62 (1H, broad), 5.61 (1H, d), 5.33 (2H, m), 3.04 (1H, broad), 2.43 (3H, S);

MS: m/e 390 ($M^+$), 332, 290, 278, 235, 218; feature: colorless wax.

EXAMPLE 6(a)~6(d)

The compounds shown in Table V was obtained by the same procedure as example 6, with using suitable

EXAMPLE 7

Amide of (5Z)-7-[(1R, 2S, 3S, 4S)-3-tosylaminobicyclo [2.2.1] heptan-2-yl]hept-5-enoic acid and glycine

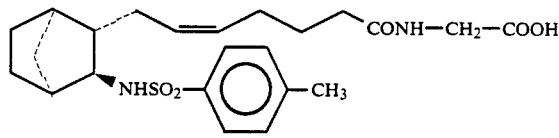

(5Z)-7-[(1R, 2S, 3S, 4S)-3-tosylaminobicyclo [2.2.1] heptan-2-yl]hept-5-enoic acid (100 mg, prepared in reference example 21), glycine tert-butyl ester hydrochloride (65.3 mg), 2-chloro-1-methylpyridinium iodide (100 mg) and triethylamine (0.22 ml) were dissolved in methylene chloride (5 ml). The mixture was stirred at a room temperature for 4 hours. The solvent was removed. The residue was purified by column chromatography on silica gel (ethyl acetate: hexane=1:2) to obtain the condensed compound. Methylene chloride (2 ml) and trifluoroacetic acid (1 ml) were added to the compound. The solution was stirred overnight and then concentrated. Trifluoroacetic acid was removed by boiling with toluene. The residue was purified by column chromatography on silica gel (methanol: methylene chloride=1:10) to obtain the title compound (56 mg) having the following physical data:

TLC (methanol: methylene chloride=1:10): Rf 0.10;

NMR: δ 7.72 (2H, d), 7.31 (2H, d), 6.30 (1H, t), 6.08 (1H, d), 5.30 (2H, m), 4.20 (1H, dd), 3.95 (1H, dd), 2.84 (1H, d), 2.43 (3H, s); MS: m/e 448 (M+), 332, 307, 293, 277, 265; feature: colorless amorphous.

EXAMPLE 7(a)–7(f)

The compounds shown in Table VI were obtained by the same procedure as described in example 7, with using the corresponding acid and suitable amino acid ester(pyrrolidine in example 7(a)).

TABLE VI

| Example No. | Structural formula | Name | TLC | MS(M/e) |
|---|---|---|---|---|
| 7 (a) |  | amide of (5Z)-7-[(1R, 2S, 3S, 4S)-3-tosylaminobicyclo[2.2.1]heptan-2-yl]hept-5-enoic acid and pyrrolidine | Rf 0.35 ethyl acetate: n-hexane = 3:1 | 444(M+), 332, 289, 272, 261, 236, 218 |
| 7 (b) |  | amide of (5Z)-7-[(1R, 2S, 3S, 4S)-3-tosylaminobicyclo[2.2.1]heptan-2-yl]hept-5-enoic acid and alanine | Rf 0.15 (methylene chloride: methanol = 10:1) | 462(M+), 444, 375, 332, 307, 291, 279 |
| 7 (c) |  | amide of (5Z)-7-[(1R, 2S, 3S, 4S)-3-tosylaminobicyclo[2.2.1]heptan-2-yl]hept-5-enoic acid and glutamic acid | Rf 0.10 (acetic acid: methanol: methylene chloride 1:10:100) | 502(M-H$_2$O), 391, 373, 347, 332, 319 |
| 7 (d) |  | amide of (5Z)-6-[(1S, 2S, 3R, 4R)-3-[N-(4-bromobenzenesulfonyl)aminomethyl]bicyclo[2.2.1]heptan-2-yl]hex-5-enoic acid and glycine | Rf 0.26 (methylene chloride: methanol) = 10:1) | 512(M+), 437, 395, 342 |
| 7 (e) |  | amide of (5Z)-6-[(1S, 2S, 3R, 4R)-3-[N-(4-bromobenzenesulfonyl)aminomethyl]bicyclo[2.2.1]heptan-2-yl]hex-5-enoic acid and alanine | Rf 0.28 (methylene chloride: methanol) = 10:1) | 526(M+), 437, 395 |
| 7 (f) |  | amide of (5Z)-6-[(1S, 2S, 3R, 4R)-3-[N-(4-bromobenzenesulfonyl)aminomethyl]bicyclo[2.2.1]heptan-2-yl]hex-5-enoic acid and glutamic acid | Rf 0.17 (acetic acid: methanol: methylene chloride 1:10:100) | 584(M+), 566, 455, 437, 395 |

EXAMPLE 8

Amide of (5Z)-7-[(1R, 2S, 3S, 4S)-3-tosylaminobicyclo [2.2.1] heptan-2-yl]hept-5-enoic acid and lysine

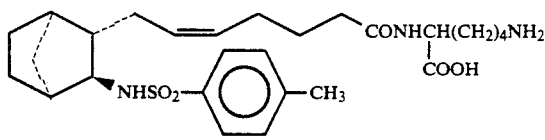

Oxalyl chloride (2 ml) was added to (5Z)-7-[(1R, 2S, 3S, 4S)-3-tosylaminobicyclo [2.2.1] heptan-2-yl]hept-5-enoic acid (100 mg, prepared in reference example 21). The mixture was stirred at a room temperature for 1 hour. Excess oxalyl chloride was removed in vacuo to obtain an acid chloride.

Next, tetrahydrofuran (4 ml) and 4N aqueous solution of sodium hydroxide (1ml) were added to ε-t-butylcarbonyl-L-lysine (492 ml). The solution was cooled to 0° C. Acid chloride prepared before dissolved in anhydrous tetrahydrofuran (2 ml) was added dropwise to the solution. The reaction solution was stirred enough for 20 mins, acidified with 1N hydrochloric acid and then extracted with ethyl acetate. The ethyl acetate layer was dried over magnesium sulfate, filtrated and concentrated. The residue was purified by column chromatography on silica gel (methanol: methylene chloride = 1:20→1:10) to obtain the condensed compound. The obtained condensed compound was dissolved in methylene chloride (2 ml). Trifluoroacetic acid (1 ml) was added to the solution. The mixture was stirred at a room temperature for 3 hours. The solvent was removed by evaporation. The residue was purified by column chromatography on silica gel (methanol: methylene chloride = 1:10→1:5→2:3) to obtain the title compound (97.4 mg) having the following physical data.

TLC (methanol: methylene chloride = 2:3): Rf = 0.20;
NMR: δ 7.73 (2H, d), 7.31 (2H, d), 5.23 (2H, m), 2.91 (4H, m), 2.43 (3H, s);
MS: m/e 501 (M-18), 346, 218; feature: pale yellow amorphous.

EXAMPLE 8(a)

The following compound was obtained by the same procedure as example 8 with using the carboxylic acid prepared in example 1(y).

Amine of (5Z)-6-[(1S,2S, 3R, 4R)-3-[N-(4-bromobenzenesulfonyl)aminomethyl]bicyclo[2.2.1]heptan-2-yl]hex-5-enoic acid and lysine.

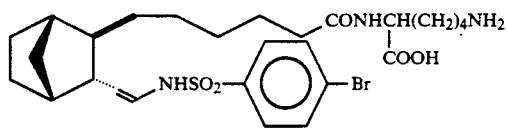

TLC (methylene chloride: methanol = 3:2): Rf 0.31;
MS: m/z 583 (M+), 565, 455.

EXAMPLE 9

(5Z)-6-[(1S,2S, 3R, 4R)-3-[N-(4-bromobenzenesulfonyl)aminomethyl]bicyclo[2.2.1]heptan-2-yl]hex-5-en-1-ol

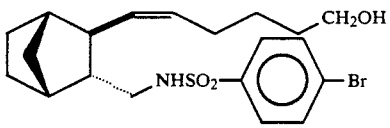

(5Z)-6-[(1S,2S, 3R, 4R)-3-[4-(4-bromobenzene sulfonyl) aminomethyl]bicyclo[2.2.1]heptan-2-yl]hex-5-enoic acid prepared in reference example 1(y) (100 mg) was dissolved in methanol (5 ml). A solution of diazomethane in ether was added to the solution till the reaction mixture showed yellow. The mixture was concentrated. The obtained residue was dissolved in anhydrous THF (10 ml). The solution was cooled to −78° C. Lithium aluminum hydride (17 mg) was added to the solution with stirring. The temperature of the reaction mixture was raisen to 0° C. gradually. The mixture was poured into 1N HCl (20 ml). The mixture was extracted with ether (20 ml) three times. The extract was dried over magnesium sulfate and then filtered. The filtrate was concentrated. The obtained residue was purified by column chromatography on silica gel (ethyl acetate: n-hexane = 1:2) to obtain the title compound (80 mg) having the following physical data.

TLC (ethyl acetate: n-hexane = 2:1): Rf 0.52;
NMR: δ 1.04~2.20 (17H), 2.78~3.11 (2H), 3.64 (2H), 4.33 (1H, t), 5.22 (2H), 7.64 (2H), 7.71 (2H);
MS: m/z 442 (M+1), 423, 354, 342, 248, 222, 206, 178, 155.

EXAMPLE 10

(5Z)-6-[(1R, 2R, 3R, 4S)-3-[N-(4-bromobenzenesulfonylaminomethyl]bicyclo[2.2.1]heptan-2-yl]hex-5-enyl acetate

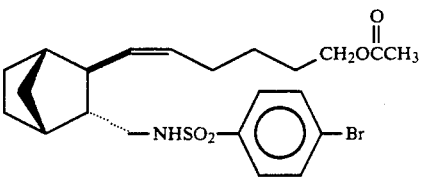

Anhydrous acetic acid (2 ml) and pyridine (2ml) were added to (5Z)-6-[(1R, 2R, 3R, 4S)-3-[4-(4-bromobenzenesulfonylaminomethyl]bicyclo[2.2.1]heptan-2-yl]hex-5-enoic acid (prepared in example 1(y), 100 mg). The mixture solution was stirred at a room temperature for 2 hours. The reaction mixture was poured into 2N hydrochloric acid (20 ml). The solution was extracted with ethyl acetate (20 ml) three times. The extract was washed with a saturated aqueous solution of sodium bicarbonate followed by saturated brine (20 ml). The extract was dried over magnesium sulfate, filtered and concentrated. The obtained residue was purified by column chromatography on silica gel (n-hexane: ethyl acetate = 4:1) to obtain the title compound (103 mg) having the following physical data.

TLC (n-hexane: ethyl acetate = 4:1): Rf 0.19;
MS: m/z 483(M+), 423, 342, 275, 264.
The following compound was obtained by the same procedure as example 10, with using anhydrous benzoic acid instead of anhydrous acetic acid.

EXAMPLE 10(a)

(5Z)-6-[(1R, 2R, 3R, 4S)-3-[N-(4-bromobenzenesulfonyl)aminomethyl]bicyclo[2.2.1]heptan-2-yl]hex-5-enyl benzoate

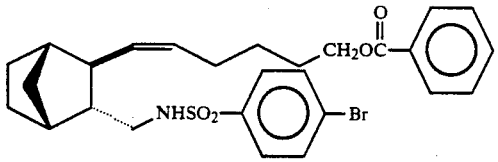

TLC (n-hexane: ethyl acetate=4:1): Rf 0.23;
NMR: δ 8.00 (2H, m), 7.70 (4H, m), 7.42 (3H, m), 5.25 (2H, m), 4.35 (3H, m), 2.97 (2H, m), 2.17~1.00 (16H);
MS: m/z 545 (M+), 423, 342, 275.

| Formulation example 1 Preparation of tablets | |
| --- | --- |
| (5Z)-6-[(1R, 3S)-3-(4-bromobenzenesulfonylamino)cyclopentyl]hex-5-enoic acid | 10 g |
| Cellulose calcium glucolate (disintegrating agent) | 200 mg |
| Magnesium stearate (lubricating agent) | 100 mg |
| Microcrystaline cellulose | 9.7 g |

The compounds described above were admixed in conventional method and punched out to obtain 100 tablets each containing 100 mg of active ingredient.

Formulation example 2

Preparation of injections 5(Z)-6-[(1R, 3S)-3-(4-bromobenzenesulfonylamino)cyclopentyl]hex-5-enoic acid (5 g) and mannitol (50 g) were dissolved by adding distilled water. Then, distilled water was added thereto to make the total volume 500 ml. The solution was filtrated by a bacteria-retaining filter. The solution was placed in 5 ml portions in 10 ml vials in the usual way and freeze-dried to obtain 100 vials each containing 50 mg of active ingredient.

What is claimed is:
1. A sulfonamide derivative of the formula:

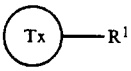

wherein $R^1$ represents
(i) $COOR^{11}$,
(ii) $CH_2OR^{12}$ or
(iii) $CONR^{13}R^{14}$,
wherein $R^{11}$ represents a hydrogen atom, alkyl group of from 1 to 20 carbon atom(s), mono-, bi- or tri-aromatic carbocyclic ring(s) containing not more than 15 carbon atoms which may be partially or fully saturated, wherein the said carbocyclic ring(s) is unsubstituted or substituted by an alkyl or alkoxy group of from 1 to 4 carbon atom(s) or halogen atom, or cholesterol,
$R^{12}$ represents a hydrogen atom or $COR^{15}$,
$R^{13}$ and $R^{14}$ each represent a hydrogen atom or alkyl group of from 1 to 4 carbon atom(s) or $NR^{13}R^{14}$ represents an amino acid residue selected from glycine, alanine, valine, isoleucine, leucine, serin, threonine, proline, asparagine, glutamine, methionine, phenylalanine, tyrosine, aspartic acid, glutamic acid or lysine or a heterocyclic ring selected from the group consisting of pyrrole, imidazole, pyrazole, pyrroline, pyrrolidine and imidazolidine, or $R^{15}$ represents an alkyl group of from 1 to 4 carbon atom(s) or phenyl group,

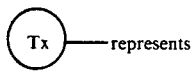 represents

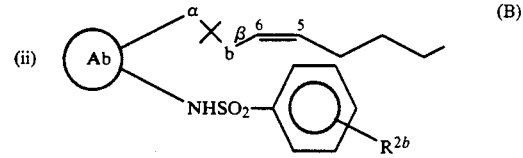

wherein

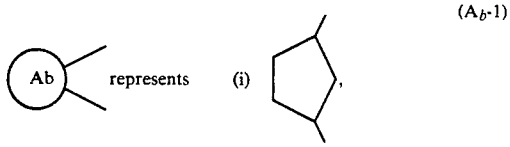 represents

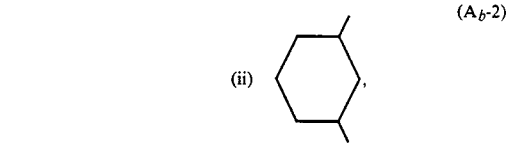

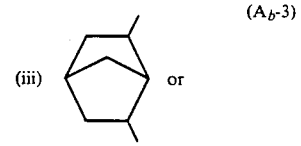

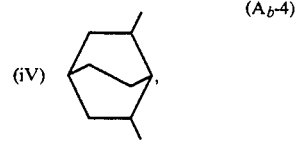

$X_b$ represents
(i) bond,
(ii) alkylene group of from 1 to 4 carbon atoms or
(iii) alkenylene group of from 2 to 4 carbon atoms (with the proviso that $\overset{\alpha}{-}CH=CHCH_2\overset{\beta}{-}$ and $\overset{\alpha}{-}CH_2CH=CHCH_2\overset{\beta}{-}$ are excluded), $R^{2b}$ represents
(i) hydrogen atom,
(ii) halogen atom or
(iii) alkyl group of from 1 to 4 carbon atom(s), the configuration of a double bond between $C_5$ and $C_6$ in the formula (B) is cis, cyclodextrin clathrates thereof, or non-toxic salts thereof in the case that $R^{11}$ represents a hydrogen atom or $NR^{13}R^{14}$ represents an amino acid residue selected from glycine, alanine, valine, isoleucine, leucine, serin, threonine, proline, asparagine, glutamine, methionine, phenylalanine, tyrosine, aspartic acid, glutamic acid or lysine.

2. A derivative according to claim 1, wherein Ab represents the formula (Ab-1) or (Ab-2).

3. A derivative according to claim 1, which is
(5Z)-6-[3-(4-bromobenzenesulfonylamino)cyclopentyl]hex-5-enoic acid,
(5Z)-8-[3-tosylaminocyclopentyl]oct-5-enoic acid,
(5Z, 7Z)-8-[3-tosylaminocyclopentyl]otc-5,7-dienoic acid,
(5Z)-6-[3-(4-bromobenzenesulfonylamino)cyclohexyl]hex-5-enoic acid,
(5Z)-6-[6-(4-bromobenzenesulfonylamino)bicyclo[2.2.1]heptan-2-yl]hex-5-enoic acid,
(5Z)-7-[6-tosylaminobicyclo[2.2.1]heptan-2-yl]hept-5-enoic acid,
(5Z)-6-[6-(4-bromobenzenesulfonylamino)bicyclo[2.2.2]octan-2-yl]hex-5-enoic acid,
(5Z)-6-[3-tosylaminocyclopentyl]hex-5-enoic acid, methyl(5Z)-6-[6-(4-bromobenzenesulfonylamino)bicyclo[2.2.1]heptan-2-yl]hex-5-enoate,
octyl(5Z)-6-[3-(4-bromobenzenesulfonylamino)cyclopentyl]hex-5-enoate,
methyl(5Z)-6-[3-(4-bromobenzenesulfonylamino)cyclopentyl]hex-5-enoate,
ethyl(5Z)-6-[3-(4-bromobenzenesulfonylamino)cyclopentyl]hex-5-enoate,
isopropyl(5Z)-6-[3-(4-bromobenzenesulfonylamino)cyclopentyl]hex-5-enoate,
methyl(5Z)-6-[3-(4-bromobenzensulfonylamino)cyclopentyl]hex-5-enoate or
(5Z)-6-[3-(4-bromobenzensulfonylamino)cyclopentyl]hex-5-enomide.

4. A derivative according to claim 1, wherein $NR^{13}R^{14}$ represents said heterocyclic ring selected from the group consisting of pyrrole, imidazole, pyrazole, pyrroline, pyrrolidine and imidazolidine.

5. A pharmaceutical composition for the prevention and/or treatment of hypertension, thrombus, cerebral apoplexy, asthma, cardiac infarction, angina pectoris, cerebral infarction, and acute cardiac diseases, which comprises, as active ingredient, an effective amount of at least one compound of the formula (I) depicted in claim 1, wherein various symbols are as defined in claim 1, or a cyclodextrin clathrate thereof, or, when $R^1$ represents a hydrogen atom, a non-toxic salt thereof, together with a pharmaceutical carrier or coating.

6. A method for the prevention and/or treatment of hypertension, thrombus, cerebral apoplexy, asthma, cardiac infarction, angina pectoris, cerebral infarction, and acute cardiac diseases, which comprise the oral, rectal, or parenteral administration of an effective amount of a compound as claimed in claim 1, a cyclodextrin clathrate thereof, or when $R^1$ is formula (I) depicted in claim 1 represents a hydrogen atom, a non-toxic salt thereof.

* * * * *